United States Patent
Walsh et al.

(10) Patent No.: US 11,931,073 B2
(45) Date of Patent: Mar. 19, 2024

(54) MEDICAL IMAGING DEVICES, SYSTEMS, AND METHODS

(71) Applicant: Boston Scientific Scimed, Inc., Maple Grove, MN (US)

(72) Inventors: Kevin Walsh, Wellesley, MA (US); Jeremy DiTullio, North Grafton, MA (US); Austin G. Johnson, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 101 days.

(21) Appl. No.: 16/875,395

(22) Filed: May 15, 2020

(65) Prior Publication Data
US 2020/0359996 A1 Nov. 19, 2020

Related U.S. Application Data

(60) Provisional application No. 62/849,311, filed on May 17, 2019, provisional application No. 62/849,307, (Continued)

(51) Int. Cl.
*A61B 17/34* (2006.01)
*A61B 8/00* (2006.01)
(Continued)

(52) U.S. Cl.
CPC ............ *A61B 17/3478* (2013.01); *A61B 8/12* (2013.01); *A61B 8/445* (2013.01); *A61B 8/4455* (2013.01);
(Continued)

(58) Field of Classification Search
CPC .... A61B 2090/3925; A61B 2010/0208; A61B 8/12; A61B 8/445; A61B 2010/045; A61M 25/0026; A61M 2205/586
See application file for complete search history.

(56) References Cited

U.S. PATENT DOCUMENTS 5,056,529 A * 10/1991 de Groot ................ A61B 10/04
600/567
5,437,283 A * 8/1995 Ranalletta ............... A61B 8/12
600/463

(Continued)

FOREIGN PATENT DOCUMENTS

WO 2017212332 A1 12/2017

OTHER PUBLICATIONS

International Search Report and Written Opinion for the International Patent Application No. PCT/US2020/033152, dated Aug. 14, 2020, 12 pages.

*Primary Examiner* — Katherine L Fernandez
*Assistant Examiner* — Brooke Lyn Klein
(74) *Attorney, Agent, or Firm* — Seager, Tufte & Wickhem, LLP

(57) ABSTRACT

The present disclosure relates generally to medical imaging devices, such as a real-time visualization and diagnostic and/or therapeutic tool assembly, which may include an ergonomic handle and catheter configured for dual-function use during a medical procedure. By way of non-limiting example, the medical device may be configured for use with a probe, such as one disposed at the distal end of the catheter, and delivered within a bronchoscope working channel to provide real-time visualization (e.g., radial ultrasound imaging) and manipulation (e.g., diagnostic biopsy sampling) of pulmonary nodules in peripheral regions of the lung. As disclosed herein, in various embodiments, one or more components of the medical imaging device may be configured to position a catheter with a first tool/instrument (e.g., a biopsy needle) within a peripheral region of the lung while maintaining real-time visualization of the pulmonary nodule (e.g., with a second tool/instrument, such as a radial ultrasound probe).

11 Claims, 32 Drawing Sheets

Related U.S. Application Data filed on May 17, 2019, provisional application No. 62/849,649, filed on May 17, 2019.

(51) Int. Cl.
| | |
|---|---|
| *A61B 8/08* | (2006.01) |
| *A61B 8/12* | (2006.01) |
| *A61B 10/02* | (2006.01) |
| *A61B 10/04* | (2006.01) |
| *A61B 17/00* | (2006.01) |
| *A61B 17/24* | (2006.01) |
| *A61B 90/00* | (2016.01) |
| *A61M 25/00* | (2006.01) |

(52) U.S. Cl.
CPC .......... *A61B 8/4461* (2013.01); *A61B 8/4494* (2013.01); *A61B 8/5238* (2013.01); *A61B 8/54* (2013.01); *A61B 10/0233* (2013.01); *A61B 10/04* (2013.01); *A61B 17/00234* (2013.01); *A61B 17/24* (2013.01); *A61B 17/3415* (2013.01); *A61B 90/39* (2016.02); *A61M 25/0026* (2013.01); *A61B 2010/0208* (2013.01); *A61B 2010/045* (2013.01); *A61B 2017/0034* (2013.01); *A61B 2017/00809* (2013.01); *A61B 2017/242* (2013.01); *A61B 2017/3413* (2013.01); *A61B 2090/3925* (2016.02); *A61M 2205/586* (2013.01)

(56) References Cited

U.S. PATENT DOCUMENTS

| | | | | |
|---|---|---|---|---|
| 5,702,344 | A * | 12/1997 | Silverstein | A61B 10/04 600/104 |
| 5,967,984 | A | 10/1999 | Chu et al. | |
| 2002/0002349 | A1 * | 1/2002 | Flaherty | A61M 25/0108 600/101 |
| 2003/0204137 | A1 * | 10/2003 | Chesbrough | A61B 8/481 600/426 |
| 2005/0096550 | A1 * | 5/2005 | Gerber | A61M 25/0084 600/464 |
| 2006/0116605 | A1 * | 6/2006 | Nakao | A61B 10/04 600/566 |
| 2009/0248142 | A1 * | 10/2009 | Perkins | A61F 2/2475 623/1.24 |
| 2010/0121218 | A1 * | 5/2010 | Mugan | A61B 10/0266 600/567 |
| 2010/0249601 | A1 * | 9/2010 | Courtney | A61B 18/18 600/463 |
| 2011/0077498 | A1 * | 3/2011 | McDaniel | A61M 25/0144 604/95.04 |
| 2012/0065467 | A1 * | 3/2012 | Moll | A61B 1/273 600/106 |
| 2013/0046316 | A1 | 2/2013 | Sullivan et al. | |
| 2013/0211379 | A1 * | 8/2013 | Clair | A61B 18/1492 604/272 |
| 2014/0296708 | A1 | 10/2014 | Flaherty et al. | |
| 2016/0346519 | A1 * | 12/2016 | Bagwell | A61B 10/0233 |
| 2017/0007203 | A1 * | 1/2017 | Courtney | A61B 8/445 |
| 2017/0043129 | A1 * | 2/2017 | Fuentes | A61M 25/0052 |
| 2017/0086746 | A1 * | 3/2017 | Ofek | A61B 5/318 |
| 2017/0143297 | A1 * | 5/2017 | Chaggares | H01L 41/00 |
| 2017/0303891 | A1 * | 10/2017 | Yamashita | A61B 8/12 |
| 2018/0161023 | A1 * | 6/2018 | Alsaidan | A61M 1/815 |
| 2018/0279994 | A1 * | 10/2018 | Schaer | A61B 8/42 |
| 2018/0280642 | A1 * | 10/2018 | Krupica | A61B 1/0125 |
| 2019/0374196 | A1 * | 12/2019 | Courtney | A61B 8/4254 |
| 2020/0359995 | A1 | 11/2020 | Walsh et al. | |
| 2020/0360054 | A1 | 11/2020 | Walsh et al. | |
| 2020/0360085 | A1 * | 11/2020 | Hancock | A61B 18/1206 |

* cited by examiner

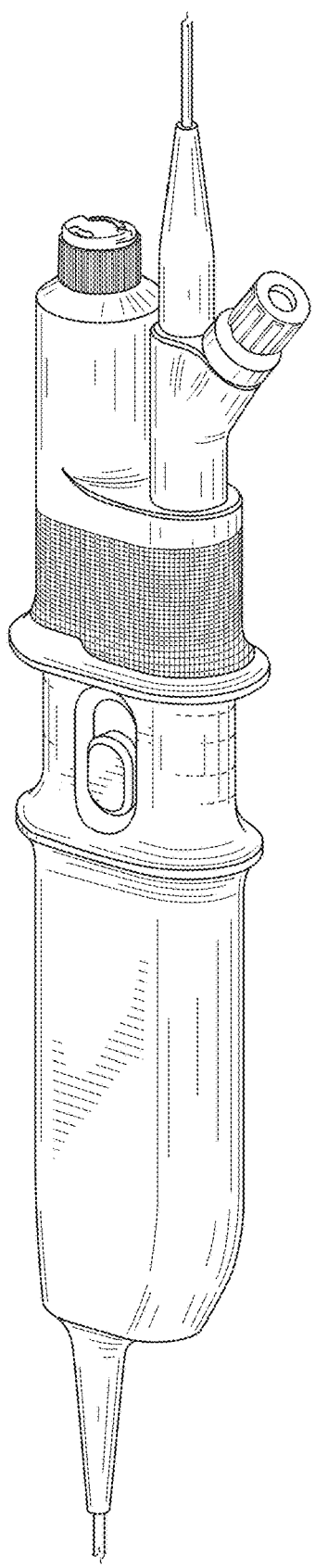
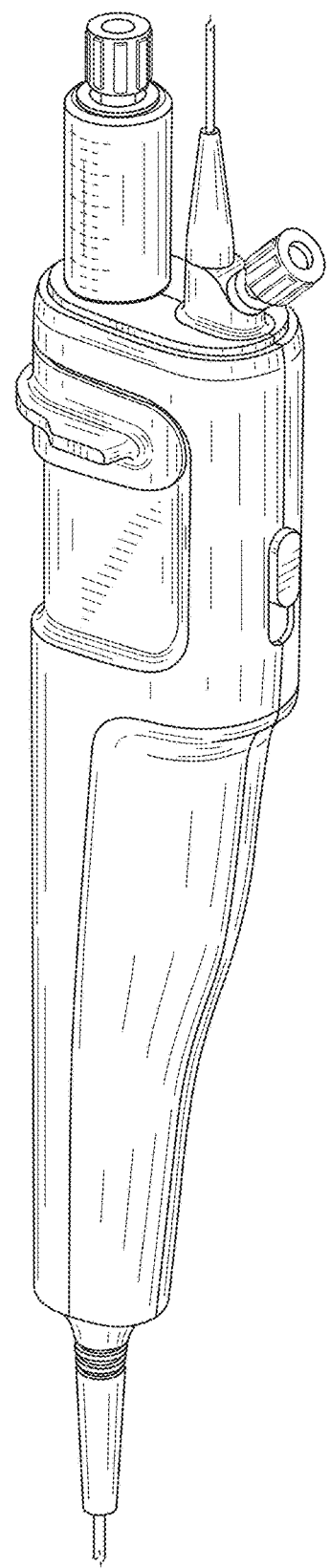
FIG. 11E
FIG. 11F

MEDICAL IMAGING DEVICES, SYSTEMS, AND METHODS

RELATED APPLICATIONS

This application claims the benefit of priority under 35 U.S.C. § 119 to U.S. Provisional Application No. 62/849,311, titled "Devices to Access Peripheral Regions of the Lung for Direct Visualization with Tool Attachment", filed on May 17, 2019, the entirety of which is incorporated herein by reference.

This application claims the benefit of priority under 35 U.S.C. § 119 to U.S. Provisional Patent Application No. 62/849,649, titled "Apparatus to Provide an Adjustable Mechanism for Radial Ultrasound Port and Flush Port", filed on May 17, 2019, the entirety of which is incorporated herein by reference.

This application claims the benefit of priority under 35 U.S.C. § 119 to U.S. Provisional Patent Application No. 62/849,307, titled "Radial Ultrasound Needle Biopsy Devices", filed on May 17, 2019, the entirety of which is incorporated herein by reference.

FIELD

The present disclosure relates generally to the field of medical devices. In particular, the present disclosure relates to devices, systems and methods that utilize imaging, and more particularly, devices, systems, and methods that integrate imaging, such as ultrasound imaging, and biopsy or other diagnostic and/or therapeutic capability in the same device.

BACKGROUND

Generally, endoscopic imaging may be performed to determine the internal characteristics of one or more target anatomies. Oftentimes, imaging is used for positioning/locating purposes, such as during a diagnostic procedure. For example, an ultrasound imaging device may be inserted into a working channel of the endoscope to image a target anatomy in an effort to position a tool through an endoscope for a procedure, such as to biopsy a pulmonary nodule. In such examples, the ultrasound imaging device may be removed from the working channel once the endoscope is positioned and a needle may be inserted into the working channel to biopsy the pulmonary nodule if the endoscope is properly positioned. Challenges with such a procedure may include maintaining location of the nodule when the probe is being exchanged with the needle (e.g., when direct visualization with a bronchoscope may not be locatable at the nodule), controlling orientation of the needle with respect to the nodule, and/or bronchoscope, and having to actuate the biopsy needle into the nodule tissue without the benefit of real-time imaging.

Biopsies are a group of medical diagnostic tests used to determine the structure and composition of tissues or cells. In biopsy procedures, cells or tissues are sampled from an organ or other body part to permit their analysis, for example under microscope. Generally, if an abnormality is found through superficial examination such as palpation or radiographic imaging, a biopsy can be performed to determine the nature of the suspected abnormality.

It is with these considerations in mind that a variety of advantageous medical outcomes may be realized by the devices, systems and methods of the present disclosure.

SUMMARY

In one aspect, the present disclosure relates to a medical device, comprising a plunger assembly, a flush port assembly, and a handle body connecting the plunger assembly to the flush port assembly. The plunger assembly may be coupled to a first tool and configured to move the first tool in a distal and a proximal direction. The flush port assembly may be coupled to a second tool and configured to rotate, at least partially, about a longitudinal axis of the second tool. In some embodiments, the flush port assembly may be configured to rotate at least 180 degrees about the longitudinal axis of the second tool. In various embodiments, the first tool may include a biopsy needle and the second tool may include a radial ultrasound probe. In several embodiments, the plunger assembly and the flush port assembly may be parallel to one another in the handle body. In many embodiments, the medical device may include a bifurcation joint in the handle body. In many such embodiments, the bifurcation joint may connect the plunger assembly to a first lumen of a dual-lumen catheter and the flush port assembly to a second lumen of the dual-lumen catheter. In various embodiments, the dual-lumen catheter may comprise a layer of braid and a layer of reflow. In some embodiments, the second tool may include an imaging transducer configured to communicatively couple with an imaging controller via a hub assembly. In some such embodiments, the imaging transducer is coupled to the hub assembly via a proximal drive cable with a first diameter and a distal drive cable with a second diameter, and the first diameter larger than the second diameter. In several embodiments, an impedance compensator connects the distal drive cable to the proximal drive cable. In many embodiments, the medical device may include a probe and a dual lumen catheter. In many such embodiments, the probe may include an imaging window and a marker, and the dual lumen catheter may connect the handle body to the probe, wherein the dual lumen catheter comprises a braided layer, wherein the braided layer is configured to axially rotate the probe within a body lumen in response to axial rotation of the handle body. In various embodiments, the medical device may include an imaging transducer extending through a first lumen of the dual lumen catheter and into the probe, the imaging transducer may be configured to generate an image of a body lumen via the imaging window, and the image of the body lumen may include an indication of the marker. In various such embodiments, the probe comprises a side port and the indication of the marker in the image of the body lumen indicates an orientation of the side port in the image of the body lumen. In some such embodiments, the side port and the marker are oriented 180 degrees apart on the probe. In several embodiments, the medical device may include a biopsy needle extending though a second lumen of the dual lumen catheter and into the probe, wherein the biopsy needle is configured to exit the probe via the side port in response to actuation of an actuation member included on the handlebody. In multiple embodiments, the medical device may include a biopsy needle extending though a second lumen of the dual lumen catheter and into the probe, wherein the biopsy needle is configured to exit the probe via the side port at an angle to the imaging window in response to actuation of an actuation member included in the handle assembly. In some embodiments, the medical device may include a dual-lumen catheter with first and second lumens. In some such embodiments, the first tool is disposed in the first lumen and the second tool is disposed in the second lumen. In various embodiments, the medical device may include a probe attached to the distal end of the dual-lumen catheter, wherein the probe includes a third lumen aligned with the first lumen of the dual-lumen catheter and a fourth lumen aligned with the second lumen of the dual-lumen catheter. In various such embodiments, the probe is attached to the distal end of the dual-lumen catheter via a reflow process. In one or more embodiments, the medical device may include an imaging controller coupled to the imaging transducer via a hub assembly and a coaxial cable. In some embodiments, the handle body comprises at least two ergonomic contours that are mirrored.

In another aspect, the present disclosure relates to a system, comprising a handle assembly, a probe, and a dual lumen catheter. The handle assembly may include a flush port and the probe may include an imaging window and a marker. The dual lumen catheter may connect the handle assembly to the probe. Further, the dual lumen catheter may comprise a braided layer configured to axially rotate the probe within a body lumen in response to axial rotation of the handle assembly. In some embodiments, the system may include an imaging transducer extending through a first lumen of the dual lumen catheter and into the probe, and the imaging transducer configured to generate an image of a body lumen via the imaging window, wherein the image of the body lumen includes an indication of the marker. In many embodiments, the probe comprises a side port and the indication of the marker in the image of the body lumen indicates an orientation of the side port in the image of the body lumen. In one or more embodiments, the side port and the marker are oriented 180 degrees apart on the probe. In many embodiments, the system includes a biopsy needle extending though a second lumen of the dual lumen catheter and into the probe, wherein the biopsy needle is configured to exit the probe via the side port in response to actuation of an actuation member included in the handle assembly.

In yet another aspect, the present disclosure relates to a system comprising a handle assembly, a probe, and a dual lumen catheter. The handle assembly may include a bifurcation joint and the probe may include an imaging window and a marker. The dual lumen catheter may connect the bifurcation joint to the probe, and be configured to axially rotate the probe within a body lumen in response to axial rotation of the handle assembly.

In yet another aspect, the present disclosure relates to an apparatus comprising a processor and a memory comprising instructions that when executed by the processor cause the processor to perform one or more of the following. In some embodiments, the memory may include instructions to cause the processor to control one or more aspects of an imaging transducer, such as generating an image based on signals received from the imaging transducer.

In yet another aspect, the present disclosure relates to a method. The method may include one or more of inserting a medical imaging device through a working channel of a bronchoscope, extending the medical imaging device past a distal end of the bronchoscope, generating an image with the medical imaging device, aligning the medical imaging device to take a biopsy of a nodule based on the image, and taking a biopsy of the nodule based on the image.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 11A-11L illustrate various exemplary handle assemblies according to one or more embodiments described herein.

DETAILED DESCRIPTION

Figure 1:
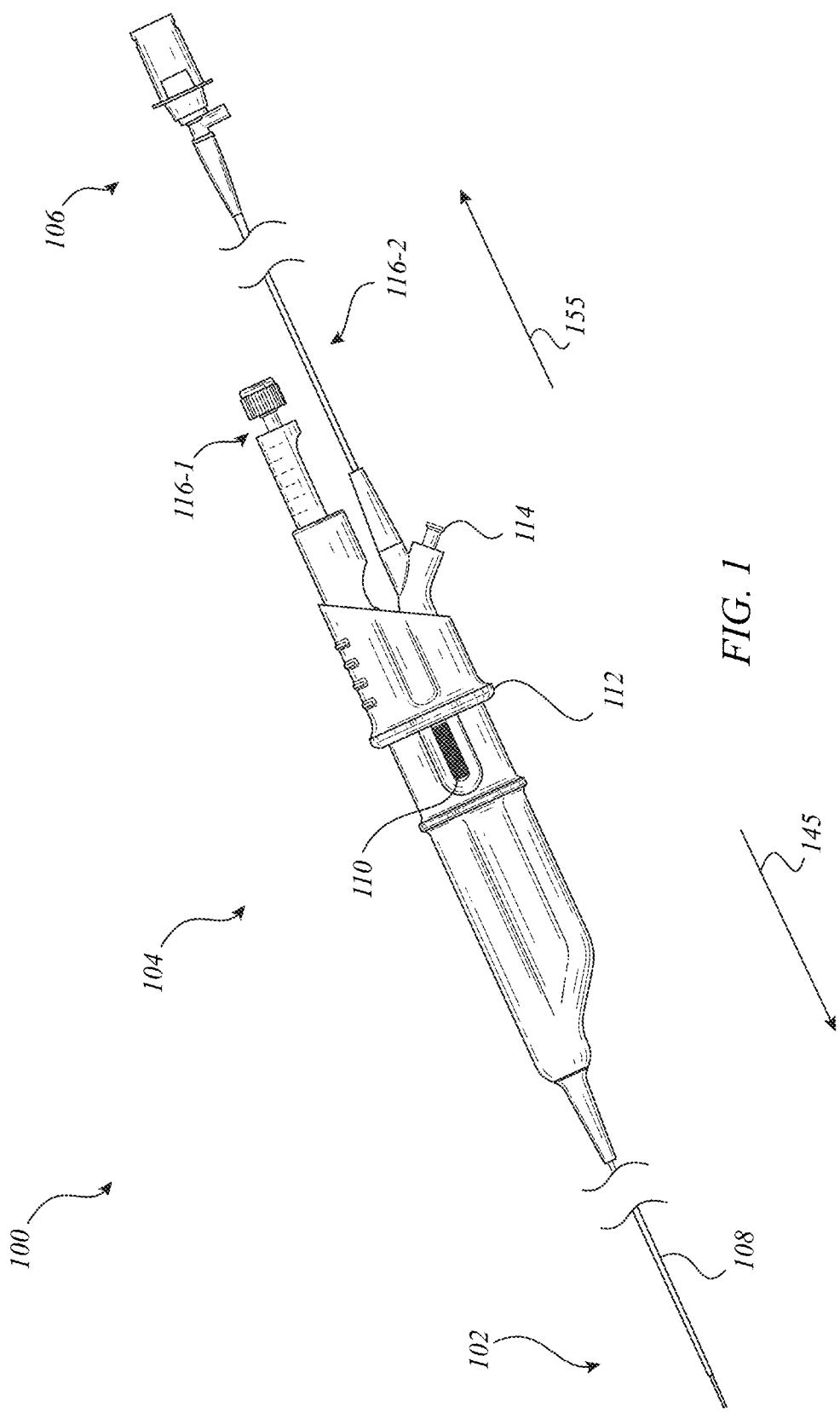
FIG. 1 illustrates an exemplary medical imaging device according to one or more embodiments described herein.

In various embodiments, the present disclosure relates generally to medical imaging devices, such as a real-time visualization and diagnostic and/or therapeutic tool assembly (e.g., an assembly with radial ultrasound imaging and biopsy needle capability) which may include an ergonomic handle and catheter configured for dual-function use during a medical procedure, such as a bronchoscopy. By way of non-limiting example, the medical device may be configured for use with a probe, such as one disposed at the distal end of the catheter, and delivered within a bronchoscope working channel to provide real-time visualization (e.g., radial ultrasound imaging) and manipulation (e.g., diagnostic biopsy sampling) of pulmonary nodules in peripheral regions of the lung. As disclosed herein, in various embodiments, one or more components of the medical imaging device may be configured to position a catheter with a first tool/instrument (e.g., a biopsy needle) within a peripheral region of the lung while maintaining real-time visualization of the pulmonary nodule (e.g., with a second tool/instrument, such as a radial ultrasound probe). In addition, or alternatively, the assembly may be configured to allow a medical professional to access, lock, and/or manipulate a tool/instrument attached thereto using a single hand.

Although embodiments of the present disclosure are described with specific reference to assemblies, systems and methods designed to provide dual-function real-time visualization and diagnostic sampling of pulmonary nodules within peripheral regions of the lung, it should be appreciated that such assemblies, systems and methods may be used to visualize and manipulate a variety of tissues within a variety of different body lumens and/or body passages for diagnostic and/or therapeutic purposes. In various embodiments described herein, direct visualization may refer to video imaging with an endoscope and real-time visualization may refer to imaging with an instrument (e.g., radial ultrasound probe) inserted through a working channel of the endoscope and past the distal end of the endoscope. Additionally, or alternatively, in one or more embodiments described herein, direct visualization may refer to imaging that utilizes the visible spectrum of light (video image) and real-time visualization may refer to imaging that does not utilize the visible spectrum of light (e.g., ultrasound imaging or infrared imaging).

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

With general reference to notations and nomenclature used herein, one or more portions of the detailed description which follows may be presented in terms of program procedures executed on a computer or network of computers. These procedural descriptions and representations are used by those skilled in the art to most effectively convey the substances of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic, or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, these manipulations are often referred to in terms, such as adding or comparing, which are commonly associated with mental operations performed by a human operator. However, no such capability of a human operator is necessary, or desirable in most cases, in any of the operations described herein that form part of one or more embodiments. Rather, these operations are machine operations. Useful machines for performing operations of various embodiments include general purpose digital computers as selectively activated or configured by a computer program stored within that is written in accordance with the teachings herein, and/or include apparatus specially constructed for the required purpose. Various embodiments also relate to apparatus or systems for performing these operations. These apparatuses may be specially constructed for the required purpose or may include a general-purpose computer. The required structure for a variety of these machines will be apparent from the description given.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1 illustrates a medical imaging device 100 according to one or more embodiments described herein. Generally, medical imaging device 100 may include a probe 102, a handle assembly 104, and a hub assembly 106. The probe 102 may be connected to the handle assembly 104 via a dual lumen catheter 108 that, among other features, facilitates the efficient and reliable use of first and second medical instruments/tools 116-1, 116-2 in conjunction with medical imaging device 100. For example, the first tool 116-1 may include a biopsy needle and the second tool 116-2 may include a radial ultrasound probe. The medical imaging device 100 may include a distal end 145 at probe 102 and a proximal end at hub assembly 106. The handle assembly 104 may include a tool lock 110, an actuation member 112, and a flush port 114. The actuation member 112 may operate the first tool 116-1 between multiple positions when tool lock 110 is unlocked. In one or more embodiments, the hub assembly 106 may interface with logic and/or control circuitry to operate at least the tool 116-2. For example, tool 116-2 may include one or more transducers for imaging that can be interfaced with a controller (e.g., imaging control 990 of FIG. 9) via hub assembly 106. In many embodiments, one or more components illustrated in FIG. 1, or described with respect thereto, may be the same or similar in construction, function, and/or appearance as one or more other components described herein. Embodiments are not limited in this context.

In various embodiments, the probe 102 may be inserted into a body lumen for diagnostic and/or therapeutic purposes. For example, medical imaging device 100 may be utilized to image and/or biopsy a nodule within a body lumen of a patient. In some embodiments, the medical imaging device 100 may be used as a stand-alone device for insertion into a body lumen. However, in additional, or alternative, embodiments the medical imaging device 100 may be configured to extend through the working channel of another medical device (e.g., a duodenoscope, endoscope, ureteroscope, bronchoscope, colonoscope, arthroscope, cystoscope, hysteroscope, etc.). For instance, medical imaging device 100 may be inserted via a bronchoscope to biopsy lung tissue.

In many embodiments, the medical imaging device 100 may be modular (include one or more modular assemblies), such as to facilitate efficient manufacturing, selectable tools, and/or reliable operation. In several embodiments, the first and second tools 116-1, 116-2 may have a parallel configuration within the handle assembly 104. In several such embodiments, the parallel configuration may facilitate reliable and intuitive single-handed operation with either hand. For example, tool lock 110 may provide ambidextrous operation (see e.g., FIGS. 5C-5E).

The flush port may facilitate fluid to be provided proximate the distal end 145, such as via the lumen of tool 116-2. In several embodiments, a fluid, such as saline, may be introduced via the flush port 114. In some embodiments, a fluid that assists with imaging may be introduced via the flush port 114, such as a conductive medium that displaces a another less conductive medium. For example, saline may be introduced to the distal end of medical device 100 via flush port 114 to enhance the propagation of sound waves from an ultrasound transducer, as tool 116-2 within probe 102, as compared to air. In some embodiments, flush port may be used to conduct other types of fluids for various other diagnostic or therapeutic purposes.

The dual lumen catheter 108 and a proximal portion of tool 116-2 (e.g., between flush port 114 and hub assembly 106) may have the same, or different, diameters. In some embodiments, a common diameter may be enabled by the fact that the proximal portion of tool 116-2 has a larger diameter drive cable than the distal portion of tool 116-2 that extends through dual lumen catheter 108.

Figure 2A:
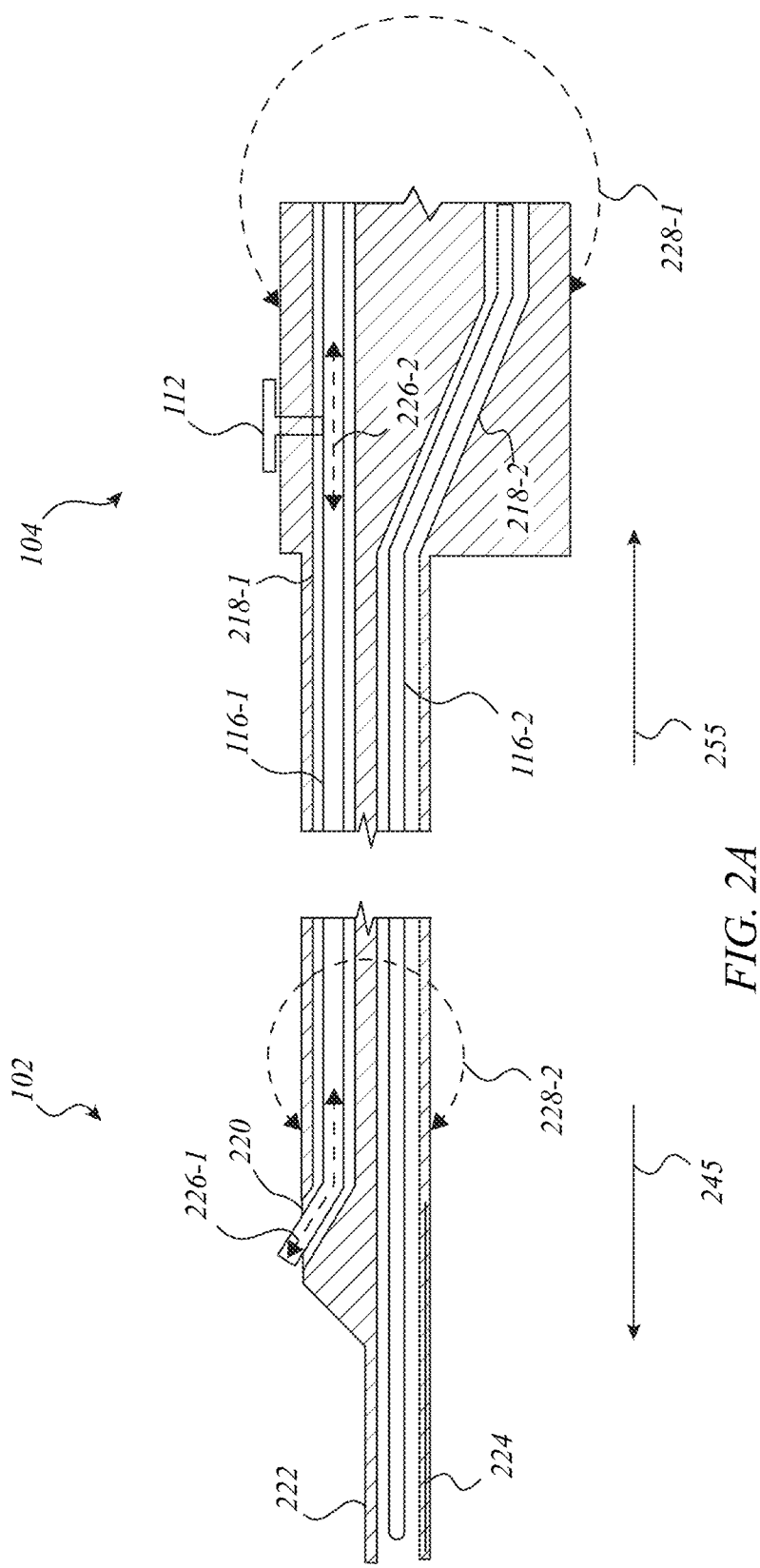
FIGS. 2A-2C illustrate various aspects of an exemplary medical imaging device according to one or more embodiments described herein.
Figure 2B:
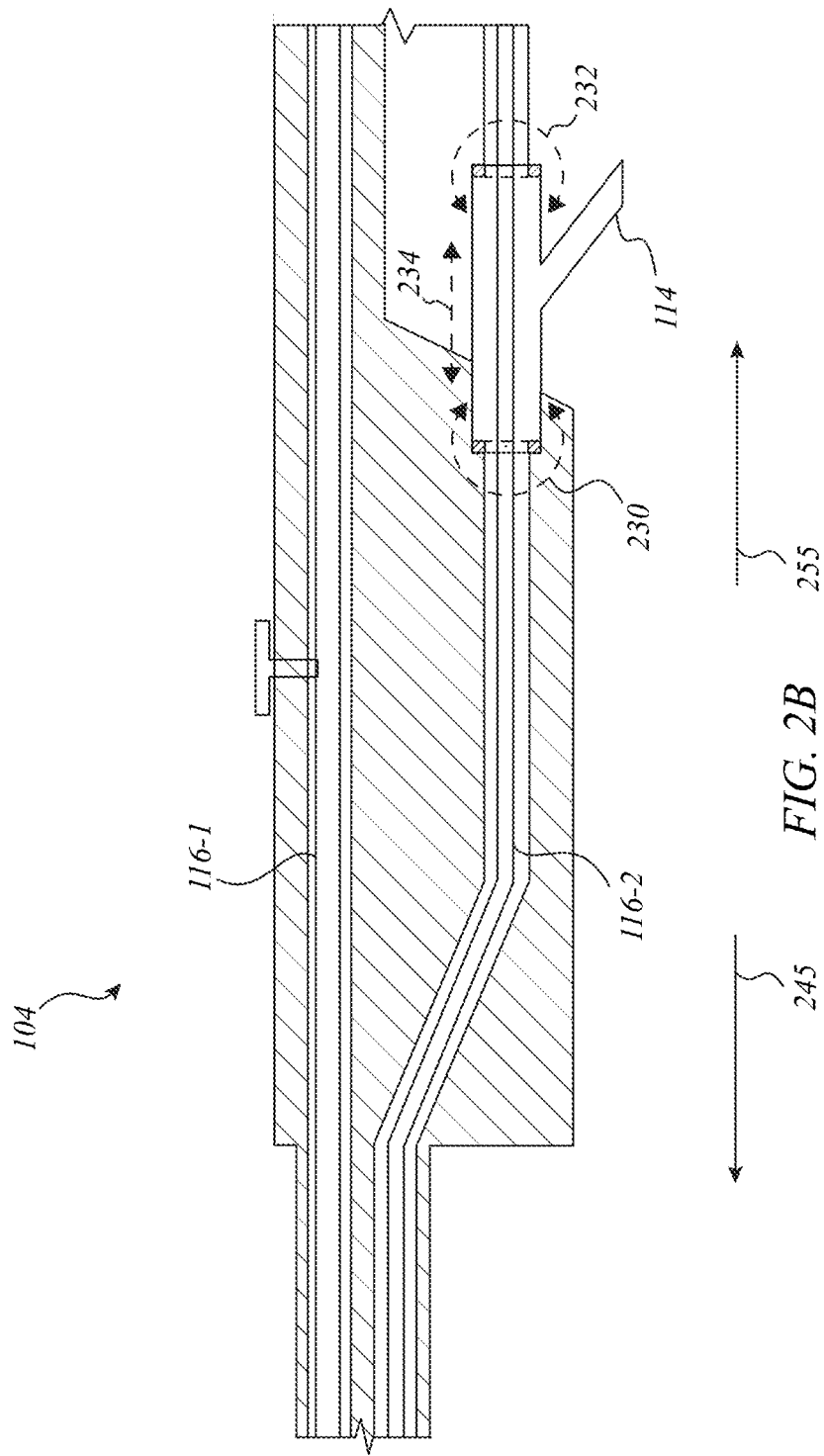
Figure 2C:
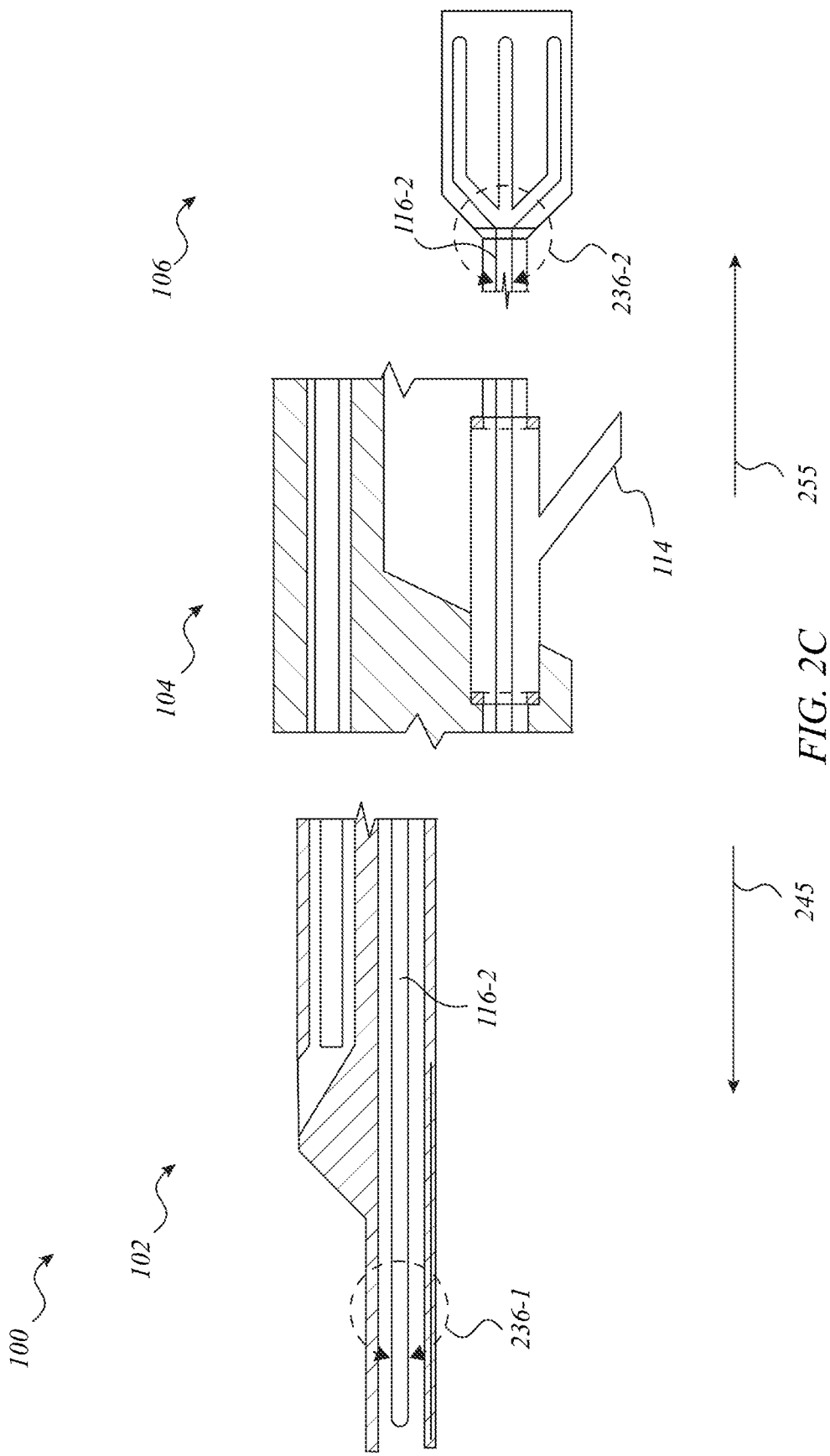

FIGS. 2A-2C illustrate various aspects of medical imaging device 100 according to one or more embodiments described herein. More specifically, FIG. 2A illustrates axial displacements and rotations of one or more of probe 102, handle assembly 104, tool 116-1, and tool 116-2. FIG. 2B illustrates axial displacements and rotations between flush port 114 and handle body 243. FIG. 2C illustrates axial rotations of tool 116-2 between the distal and proximal ends 145, 155 of medical imaging device 100. In embodiments described herein, components of the medical imaging device 100 may rotate and/or translate in reliable, intuitive, and unique and advantageous ways. For example, embodiments many include an adjustable and leak-proof flush port assembly configured for use with a bronchial radial ultrasound system to provide real-time imaging and targeting of difficult to access pulmonary nodules. For instance, the medical imaging device 100 may extend beyond the distal end of a bronchoscope to access narrower pulmonary passages than the distal end of the bronchoscope can access. In such instances, e.g., the medical imaging device may be configured to extend 15 centimeters or more beyond the distal end of the bronchoscope. Further, the adjustable flush port assembly may include an adjustable ultrasound probe and/or flush port configured to allow a physician to proximally/distally (e.g., along a longitudinal axis), laterally (e.g., along a radial axis), and/or axially (e.g., about or around a longitudinal axis) position/reposition components of the bronchial radial ultrasound system (e.g., ultrasound probe, flush port, and/or probe assembly) within a peripheral region of the lung while maintaining a leak-proof seal to simultaneously flush fluid through a lumen of the radial ultrasound probe. In many embodiments, one or more components illustrated in FIGS. 2A-2C, or described with respect thereto, may be the same or similar in construction, function, and/or appearance as one or more other components described herein. Embodiments are not limited in this context.

Referring to FIG. 2A, the probe 102 may include imaging window 222, side port 220, marker 224, and the handle assembly 104 may include actuation member 112. Additionally, lumens 218-1, 218-2 (or lumens 218) may extend approximately between the distal end 245 of probe 102 to the proximal end 255 of handle assembly 104. More specifically, the first lumen 218-1 may include a distal opening at side port 220 and the second lumen 218-2 may include a distal opening in or at the distal end 245. In some embodiments, one or more of the lumens 218 may be capped or sealed at the distal end. For example, lumen 218-2 may be capped by a balloon at the distal end 245. In various embodiments, the first tool 116-1 may be disposed in the first lumen 218-1 and the second tool 116-2 may be disposed in the second lumen 218-1. In one or more embodiments, the second tool 116-2 may include an imaging transducer. In one or more such embodiments, the first tool 116-1 may include a biopsy needle.

In the illustrated embodiment, the probe 102 includes an imaging window 222 and a marker 224. In many embodiments, imaging window 222 may refer to one or more portions of the probe 102 that are substantially transparent to the imaging energy wave lengths while marker 224 may refer to one or more portions of the probe that are relatively opaque to the imaging energy wave lengths. Marker 244 may comprise any medium that absorbs imaging energy wavelengths (e.g., ultrasound waves). For example, metal or metal alloys (e.g., stainless steel or nitinol) may be used. In some embodiments, non-metals may be used, such as air pockets embedded in the wall of the imaging window. In various embodiments, the marker 244 may be radiopaque, such as to show up on x-ray and/or fluoroscopic imaging additionally, or alternatively.

In such embodiments, marker 244 may be positioned to indicate in a generated image where the first tool 116-1 would be positioned when actuation member 112 is moved distally along axial displacement 226-2 to cause axial displacement 226-1 in tool 116-1, resulting in tool 116-1 extending out of side port 220. To position the probe 102 based on generated images, the handle assembly 104 may be rotated along axial rotation 228-1 to cause probe 102 to rotate along axial rotation 228-2. For example, the handle assembly 104 may be rotated to align the side port 220 with a target nodule based on indications of marker 224 in generated images. In some such examples, once aligned, actuation member 112 may be moved distally to cause the distal end of the first tool 116-1 to contact and/or penetrate the target nodule. In various embodiments, a marker may be embedded in a wall of a lumen, such as the wall of the second lumen 218-2. As will be appreciated, device rotation (e.g., orientation of the marker and the needle radially) may enable more efficient biopsying of eccentric nodules, e.g., when biopsying target tissue that has irregular margins, is of an asymmetric shape, does not extend around an entire circumference of the body lumen, and the like, where control or orientation and position of the needle may be more critical.

As an example, marker 224 may be oriented around the circumference of the imaging window at a known angle from side port 220. In such a case, e.g., when targeting a lung nodule for core biopsy, marker 224 may be oriented on the radial ultrasound image at the known angle from the intended biopsy site, so that a needle exiting side port 220 will be correctly aligned with the biopsy site. In a further such example, the marker 224 may be oriented on the radial ultrasound image 180 degrees across from the intended biopsy site. In many embodiments, the known angle from the intended biopsy site may be configured such that tolerances may be provided. For example, the marker 224 may be oriented on the radial ultrasound image 180±35 degrees from the intended biopsy site.

Referring to FIG. 2B, the handle assembly 104 may have a distal end 245 and a proximal end 255 and include handle body 243 and flush port 114. In many embodiments, flush port 114 may have one or more of distal axial rotation 230, proximal axial rotation 232, and proximal/distal displacement 234. In several embodiments, the flush port 114 may rotate approximately 270 degrees without contacting with the plunger assembly and/or handle body. In many embodiments, rotation of the flush port 114 may allow the flush port 114 to be positioned such that the proximal drive cable does not interfere with usage, contributing to ease of one-handed control. In various embodiments, absent any interference structures, the flush port 114 may rotate 360 degrees. Referring to FIG. 2C, the second tool 116-2 may extend from the hub assembly 106 through the flush port 114 to the distal end 245 of probe 102. In various embodiments, axial rotation 236-2 via hub assembly 106 may cause axial rotation 236-1 in probe 102. In various such embodiments, axial rotation 236-1 may enable tool 116-2 to generate a three hundred and sixty degree image and/or may allow tool 116-2 to be oriented rotationally as desired to align side port 220 and tool 116-1 with an intended target site. As will be discussed in more detail below, such as with respect to FIG. 9, hub assembly 106 may connect to an imaging controller that is able to rotate the tool 116-2 via the hub assembly 106.

Figure 3A:
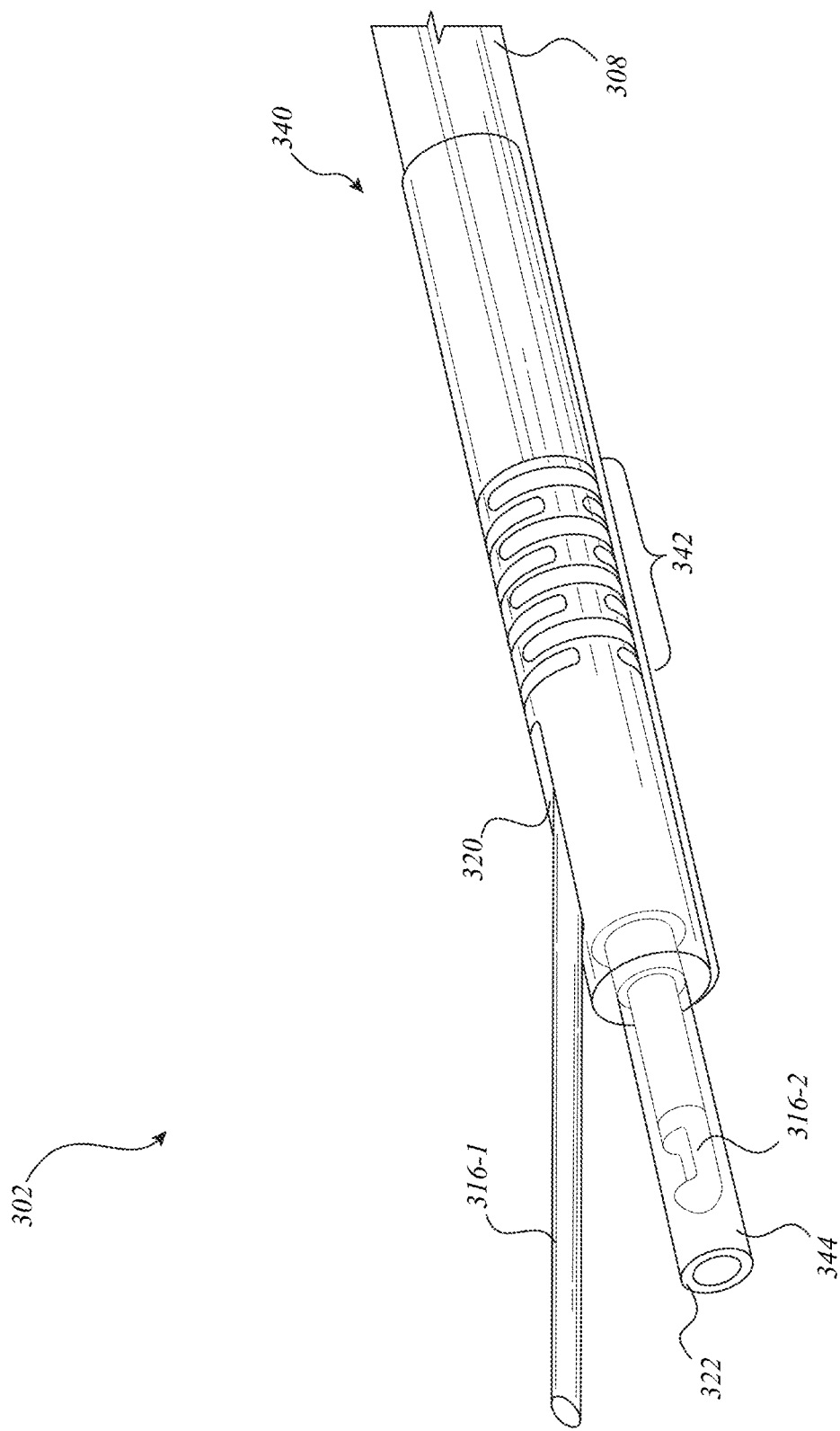
FIG. 3A-3H illustrate various aspects of an exemplary probe for a medical imaging device according to one or more embodiments described herein.
Figure 3B:
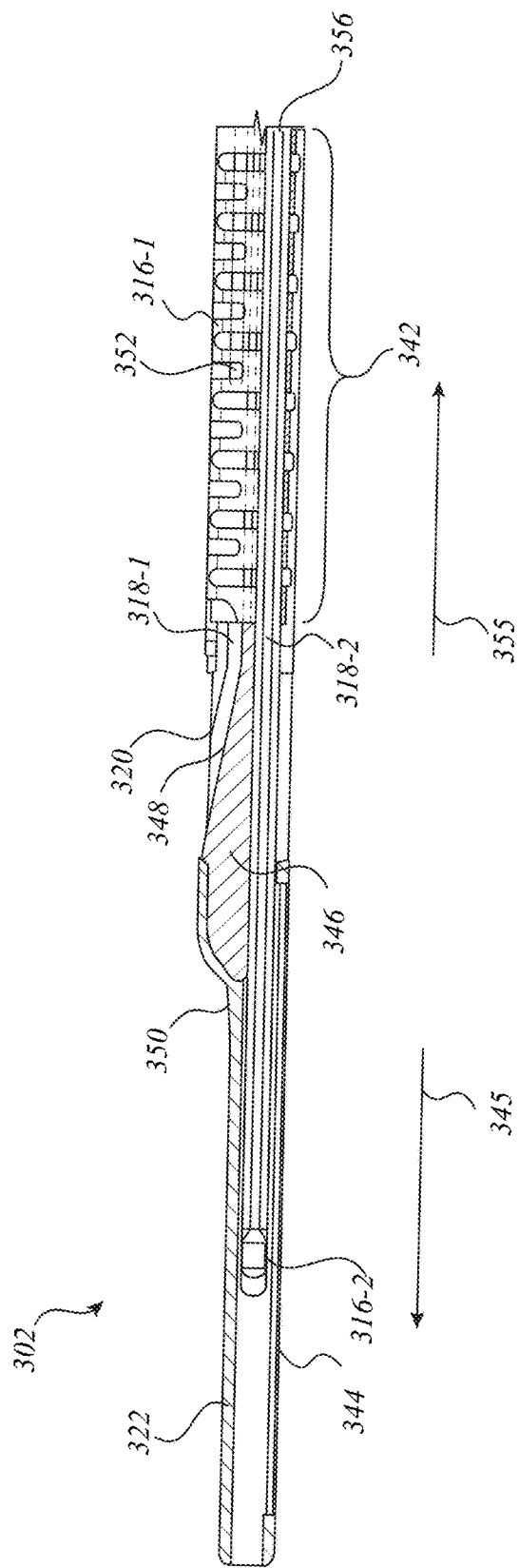
Figure 3C:
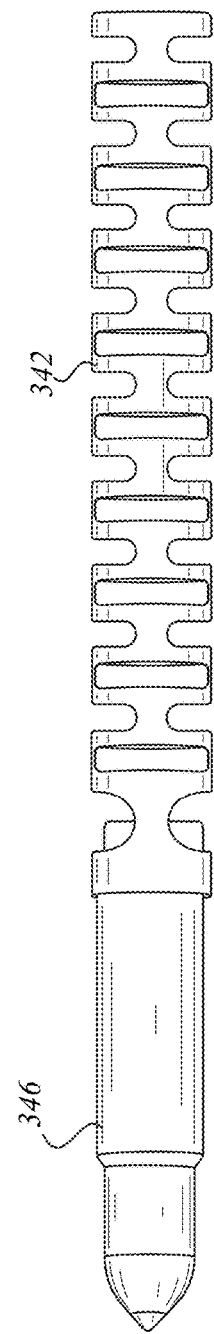
Figure 3D:
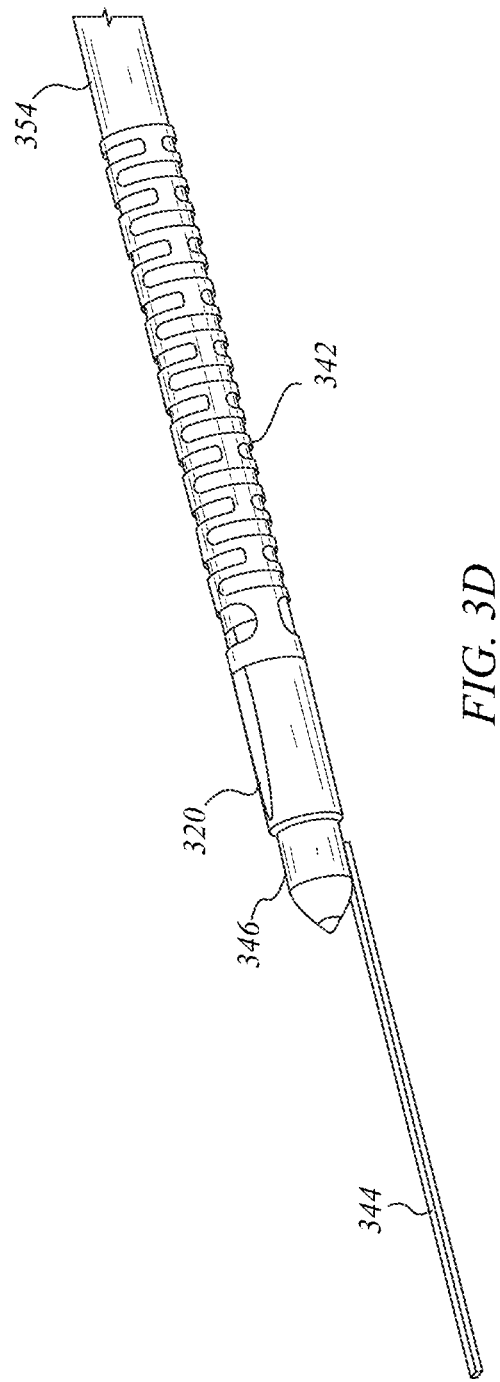
Figure 3E:
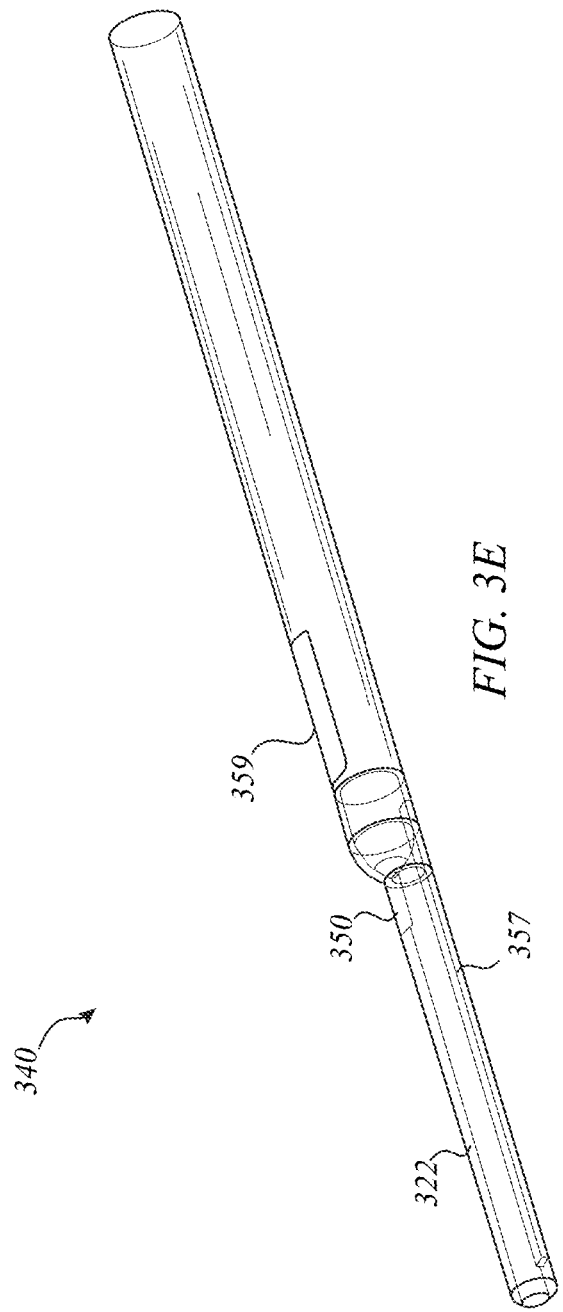
Figure 3F:
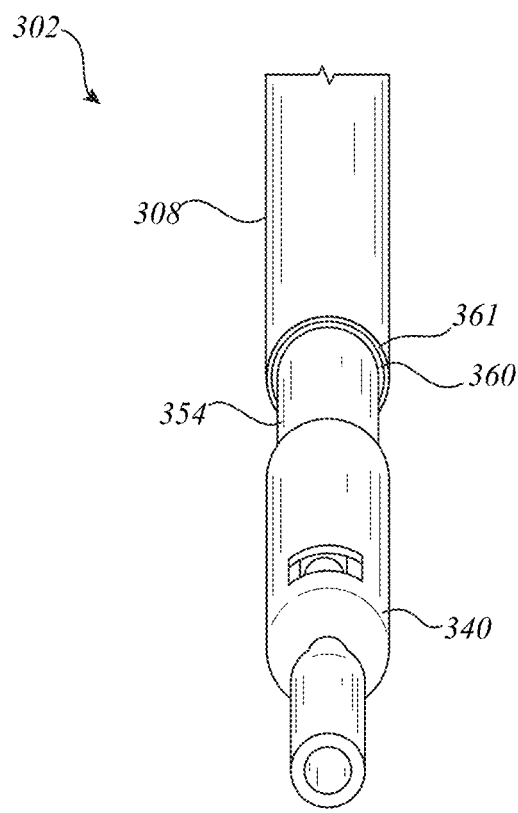
Figure 3G:
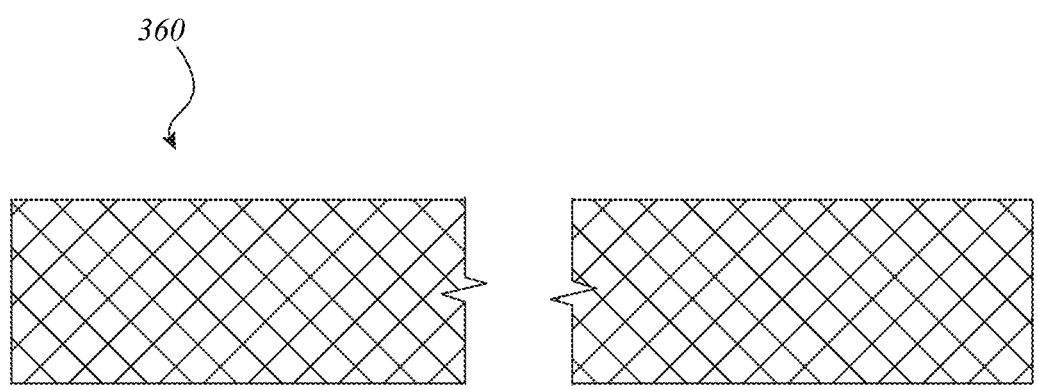
Figure 3H:
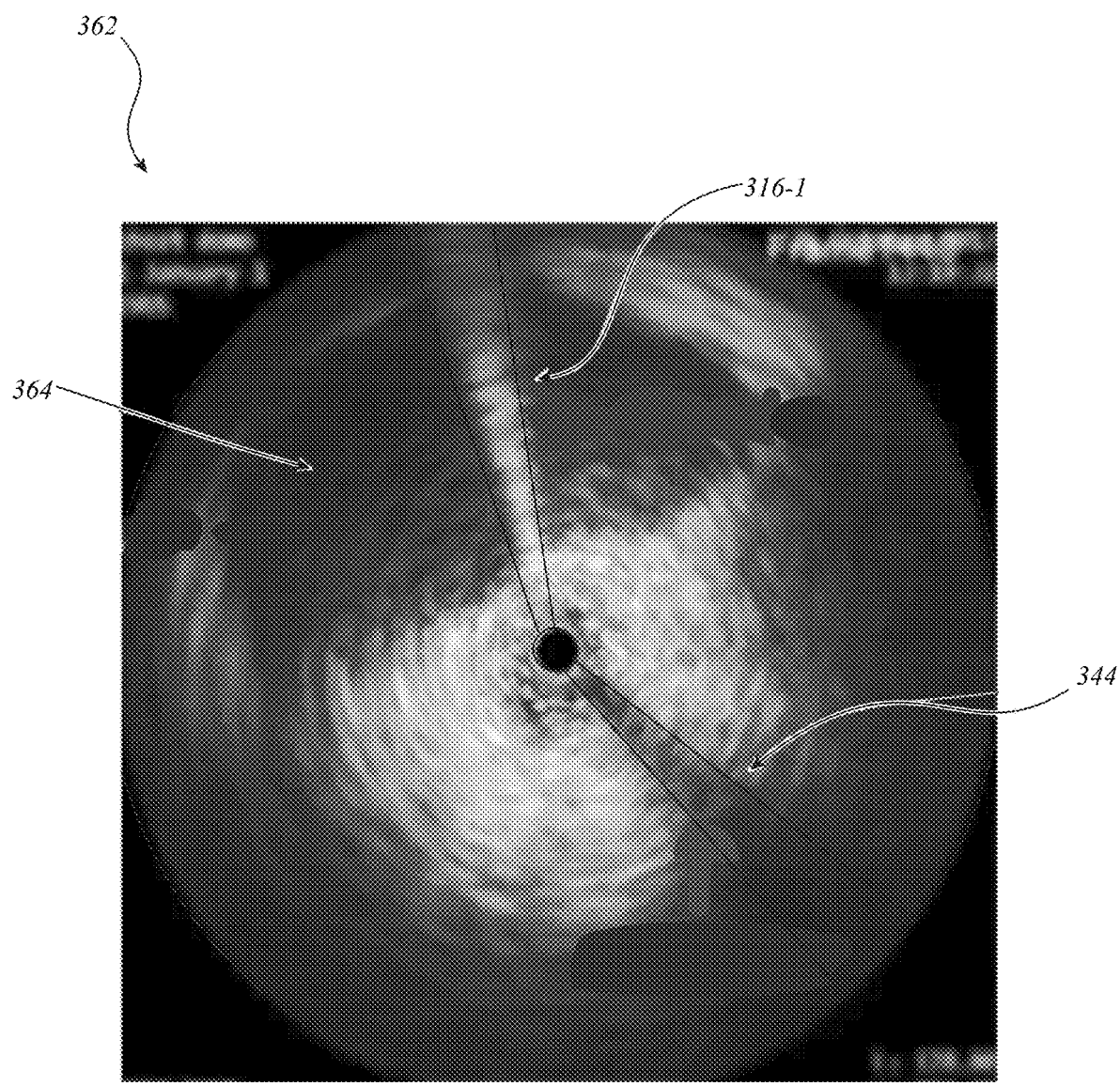

FIGS. 3A-3H illustrate various aspects of an exemplary probe 302 for a medical imaging device according to one or more embodiments described herein. More specifically, FIG. 3A illustrates a perspective view of a probe 302 and FIG. 3B illustrates a cross-sectional view of the probe 302. FIG. 3C illustrates a collar 342 in conjunction with a distal juncture 346 of the probe 302. FIG. 3D illustrates the collar 342 and distal juncture 346 in conjunction with marker 344 and tubular member 354. FIG. 3E illustrates an endcap 340 of the probe 302. FIG. 3F illustrates a front perspective view of probe 302. FIG. 3G illustrates a braid 360 utilized in the dual lumen catheter 308. FIG. 3H illustrates an example image 362 generated by the probe 302 (see e.g., FIG. 9). In embodiments described herein, components of the probe 302 may facilitate specific tissues to be targeted in reliable, intuitive, and unique and advantageous ways. For example, embodiments many include an endcap 340 disposed on the distal end of the dual lumen catheter 308. Further, the endcap 340 may align with each lumen in catheter 308, enabling needle 316-1 to exit side port 320 and ultrasound transducer 316-2 to utilize imaging window 322 and marker 344. In many embodiments, marker 344 may provide indications and/or projections of the position of needle 316-1 as it exits side port 320. This, among other features, can provide techniques to improve the efficiency, accuracy, and/or reliability with which biopsies can be taken. For instance, the real-time images with marker 344 may allow a user to determine where and from what angle the biopsy needle will exit the side port radially and/or biopsy the tissue, prior to activation, which may be particularly useful in biopsying eccentric nodules. Embodiments are not limited in this context.

Biopsies can be performed on a number of organs, tissues, and body sites, both superficial and deep, and a variety of techniques may be utilized depending on the tissue or body part to be sampled, the location, size, shape and other characteristics of the abnormality, the number of abnormalities, and patient preference. FNA (fine needle aspiration) is typically performed to sample deep tissues such as the kidney using a fine gauge needle (22 or 25 gauge) inserted percutaneously or through an endoscope under ultrasound guidance (EUS-FNA). By contrast, surgical biopsy is generally performed as an open procedure and can be either excisional (removal of an entire lesion) or incisional (removal of a piece of a lesion).

Surgical biopsies generally permit removal of more tissue than fine needle biopsies and, thus, are less prone to misdiagnosis. Open surgical procedures may be significantly more expensive than needle biopsies, may require more time for recuperation, require sutures, may leave a disfiguring scar, may require anesthesia, may carry a small risk of mortality, and may result in bleeding, infection and wound healing problems.

Fine needle biopsies, however, may carry risks of their own: the relatively small quantities of tissue sampled may not be representative of the region of interest from which it is taken, particularly when that region of interest is hard to image, or the nodule is very small, very hard, and/or eccentric. Additional difficulties may arise in the context of ultrasound-guided fine needle biopsies: fine-gauge biopsy needles are typically stiffer, and less prone to deflection, than the catheter-based endoscopic ultrasound transducers used to guide them in some EUS-FNA procedures. Thus, while it may be possible to guide the transducer to a site of interest, it may not be possible to accurately sample it if the needle is too stiff to navigate the same path through the tissue. In addition, current practice involves "blind" actuation of the biopsy needle, which may result in damage to non-target tissues or false negative results if healthy tissue is sampled inadvertently next to the intended suspect tissue site.

The difficulties of fine needle biopsies are magnified in the context of pulmonary nodule sampling, where breathing rhythm cause nodules, probes and needles to move relative to one another. It would be particularly desirable in this setting to be able to visualize the nodule and needle in real time during patient respiration to ensure accurate needle tracking and sampling. Accordingly, one or more embodiments and/or features herein may resolve or minimize these issues.

Referring to FIG. 3A, probe 302 may include endcap 340 coupled to dual-lumen catheter 308 (e.g., via overmolding and/or bonding by reflowing), needle 316-1 extending out of side port 320, imaging window 322, marker 344, collar 342, and imaging transducer 316-2. As shown in the cross-sectional view in FIG. 3B, probe 302 may include first and second lumens 318-1, 318-2, needle 316-1 with stylet 352 extending therethrough, imaging transducer 316-2 with distal cable 356, side port 320 with ramp 348, imaging window 322, collar 342, marker 344, distal juncture 346, and strain relief 350.

Referring to FIG. 3C, the distal juncture 346 may comprise a portion of the first and second lumens 318. The distal juncture 346 may include side port 320 and ramp 348. In various embodiments, the angle of the ramp 348 may be, with respect to the longitudinal axis in the proximal direction, between 0 and 90 degrees. In many embodiments, higher angles may improve nodule (e.g., an eccentric lesion) targeting, but make needle actuation more difficult. For example, the higher the angle of the ramp 348, the larger the longitudinal force required to extend the needle up the ramp 348 and out of the side port 320 to actuate the needle. Further, higher angles may require the needle to extend further out of the side port 320 to enter the field of view of the imaging transducer 316-2, limiting applicability to body lumens with larger diameters. Conversely, lower angles may require the probe 302 to be located closer to a target nodule, making it difficult to acquire biopsy samples from an eccentric nodule and/or further below the surface of the target nodule. Accordingly, the ramp angle may be selected based on a particular application. In one or more embodiments, the ramp angle may be greater than or equal to 3 degrees and less than or equal to 20 degrees. For instance, the angle of ramp 348 may be 15 degrees. The distal juncture 346 and/or collar 342 may comprise a metal or metal alloy (e.g., nickel-titanium). In some embodiments, the collar 342 is laser cut. In many embodiments, the collar 342 may provide one or more of rigidity, confinement, structure, and flexibility. As shown in FIG. 3D, a tubular member 354 may extend into the collar 342. In various embodiments, tubular member 354 may comprise a portion of the dual-lumen catheter. Marker 344 is also illustrated in FIG. 3D. Marker 344 may comprise any medium that absorbs imaging energy wavelengths (e.g., ultrasound waves). For example, metal or metal alloys (e.g., stainless steel or nitinol) may be used. In some embodiments, non-metals may be used, such as air. For example, the marker 344 may comprise a pocket of air or a plurality of air bubbles extruded into the wall of the imaging window.

Referring to FIG. 3E, endcap 340 may receive the components illustrated in FIG. 3D. Marker 344 may be disposed in marker pocket 357 and side port 320 may be aligned with port window 359. In some embodiments, marker pocket 357 may comprise a pocket of air in a wall of endcap 340. Additionally, endcap 340 include imaging window 322 and strain relief 350. In one or more embodiments, imaging window 322 may be the same or similar material as the other portions of endcap 340. In various embodiments, the strain relief 350 may limit bending caused by marker 344 and/or distal juncture 346. In various embodiments, the gap between endcap 340 and the layers of braid 360 and reflow 361 remain to allow greater flexibility.

As illustrated in FIG. 3F, dual-lumen catheter 308 may include a tubular member 354 with two lumens, a layer of braid 360, and a layer of reflow 361 over the braid 360. As shown in FIG. 3G, the braid 360 may have an overlapping, woven, two wires per band, two over/two under and/or crisscross pattern. Other patterns, weave conditions, materials, and the like, may be contemplated based on a particular application of the medical imaging device. In various embodiments, the number of crossovers per inch of braid 360 may be between 25 and 140. In some embodiments, different braid strands may be at between 60 and 120 degrees of each other, such as 90 degrees. In many embodiments, the pattern of braid 360 may be selected for a combination of flexibility and strength. In various embodiments, the braid 360 may be woven stainless steel or nitinol. In several embodiments, the braid 360 may provide torsional strength to the dual lumen catheter. In several such embodiments, the torsional strength provided by the braid 360 may enable rotation of the handle to translate into rotation of the distal end. In many embodiments, rotation of the handle may result in rotation of the distal end (e.g., the probe) with a known ratio. For example, rotation of the handle may result in 1:1, or substantially 1:1, rotation of the distal end. Further, the ability to rotate the handle and cause rotation at the distal end may facilitate targeting of nodules, such as eccentric nodules, based on real-time images with marker indications. In many embodiments, endcap 340 may be coupled to the dual lumen catheter 308 via a reflow and/or overmold process. In many embodiments, the dual lumen catheter 308 may additionally, or alternatively, include a braided layer, such as braid 360. In some embodiments, the braid 360 may utilize up to 356 different strands. For example, some embodiments may utilize 64 different strands.

Figure 9:
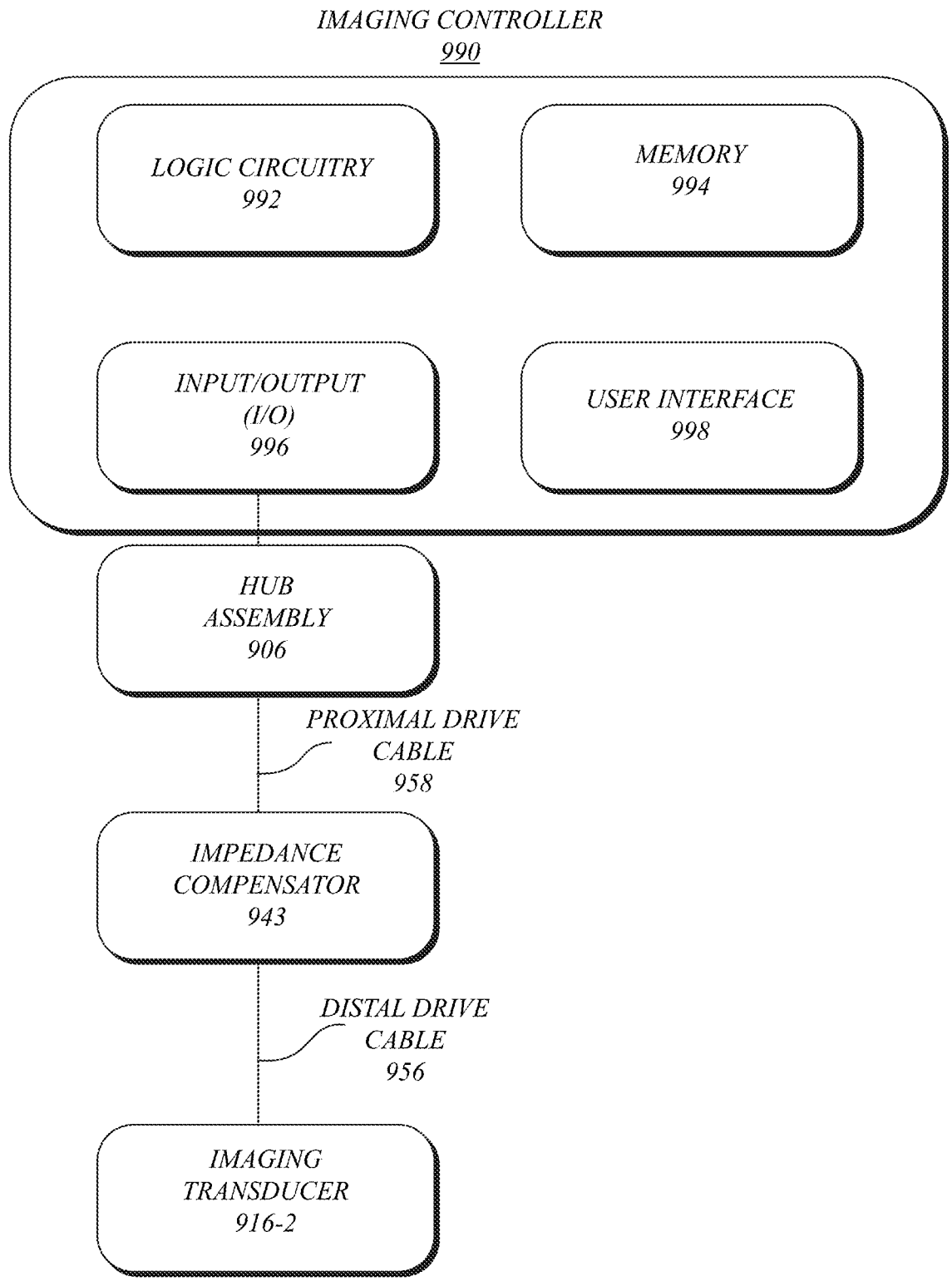
FIG. 9 illustrates various aspects of an exemplary imaging controller according to one or more embodiments described herein.

FIG. 3H illustrates an example image 362 generated by the probe 302 (see e.g., FIG. 9). The image 362 may include marker 344, needle 316-1, and nodule 364. As shown in FIG. 3H, marker 344 may provide indications and/or projections of the position of needle 316-1 as it exits side port 320 in generated images (e.g., ultrasound images). This, among other features, can provide techniques to improve the efficiency, accuracy, and/or reliability with which biopsies can be taken (e.g., the efficiency and reliability of positioning of biopsy needle to tip to optimize sampling). In the illustrated embodiment, needle 316-1 is extended to demonstrate the indication it may provide on the image compared to marker 344.

In various embodiments, marker 344 may be oriented around the circumference of the imaging window at a known angle from side port 320. In such a case, e.g., when targeting nodule 364 (e.g., an eccentric or concentric lung nodule) for core biopsy, marker 344 may be oriented on the image 362 (e.g., a radial ultrasound image) at the known angle from the intended biopsy site, so that a needle exiting side port 320 will be correctly aligned with the biopsy site. For example, in the illustrated embodiment, marker 344 may be oriented on the image 362 at 180±35 degrees from the intended biopsy site (i.e., nodule 364).

Figure 4A:
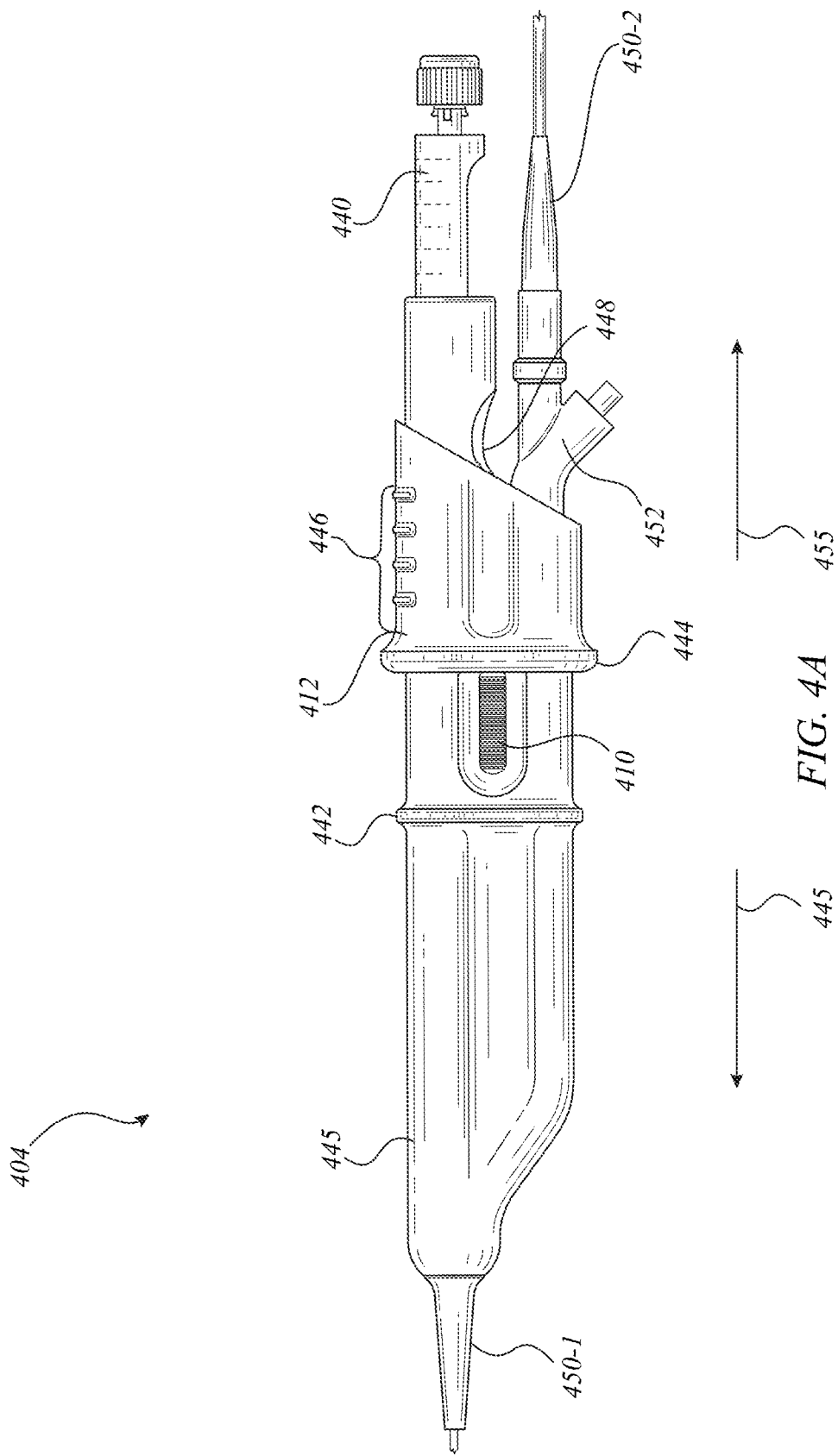
FIGS. 4A-4C illustrate an exemplary handle assembly for a medical imaging device according to one or more embodiments described herein.
Figure 4B:
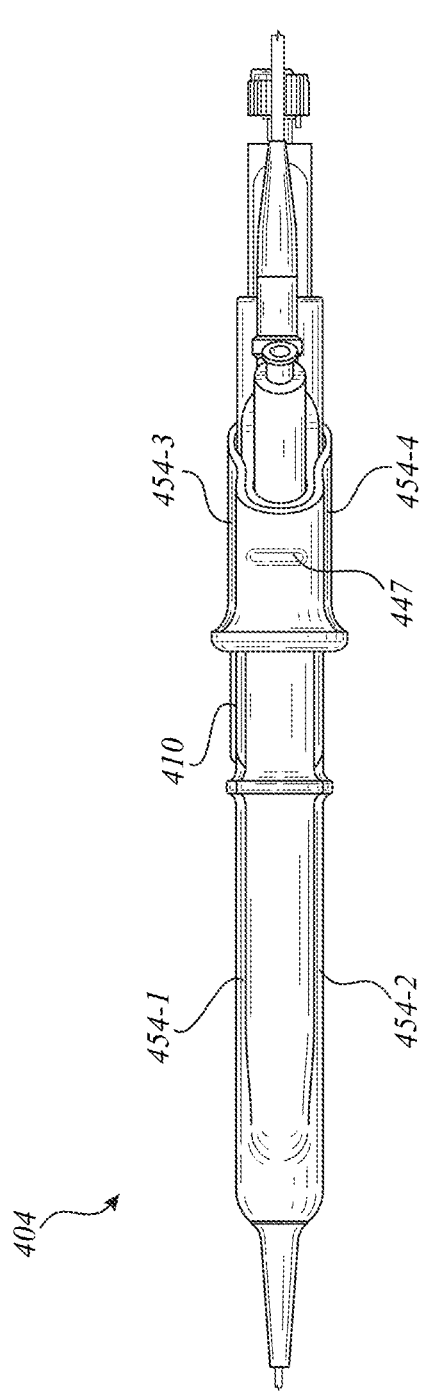
Figure 4C:
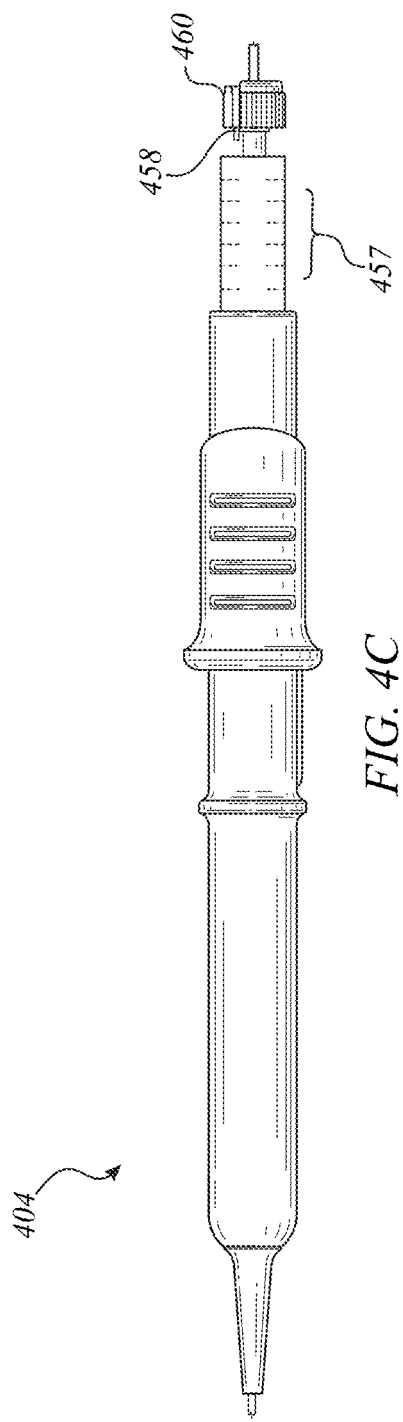

FIGS. 4A-4C illustrate an exemplary handle assembly 404 for a medical imaging device according to one or more embodiments described herein. More specifically, FIG. 4A illustrates a side view of the handle assembly 404, FIG. 4B illustrates a bottom view of the handle assembly 404, and FIG. 4C illustrates a top view of the handle assembly 404. In embodiments described herein, components of the handle assembly 404 may facilitate intuitive, ergonomic, and/or single-handed operations to target specific tissues in reliable, intuitive, and unique and advantageous ways. For example, handle assembly 404 may include one or more ergonomic contours, grip ribs, ergonomic reliefs, component positionings and/or configurations to provide convenient, comfortable, accurate, and fatigue minimizing operation. For example, tool lock 410 may provide ambidextrous operation and/or dual sided access for single-hand use (e.g., tool lock 410 is accessible by thumb while rotating the handle). In another example, grip ridge 444 and grip ribs 446, 447 may provide non slip surfaces on actuation member 412. In many embodiments, one or more components illustrated in FIGS. 4A-4C, or described with respect thereto, may be the same or similar in construction, function, and/or appearance as one or more other components described herein. Embodiments are not limited in this context.

Referring to FIG. 4A, handle assembly 404 may have distal and proximal ends 445, 455 and include handle body 443, actuation stop 442, actuation member 412 with grip ribs 446 and grip ridge 444, tool lock 410, ergonomic relief 448, strain reliefs 450-1, 450-2, plunger assembly 440, and flush port assembly 452. Referring to FIG. 4B, handle assembly 404 may include one or more ergonomic contours 454-1, 454-2, 454-3, 454-4, tool lock 410, and grip rib 447. Referring to FIG. 4C, handle assembly 404 may include displacement gauge 457, Luer lock 458, and cap 460. In some embodiments, cap 460 may be a stylet cap and/or Luer lock 458 may be a syringe connector. In various embodiments, one or more of the ergonomic contours 454, grip ribs 446, 447, ergonomic reliefs 448, and/or grip ridges 444 may be symmetrical, complementary, and/or mirrored. Further, one or more surfaces may include textures and/or coatings to promote or fight friction.

Various handle assembly embodiments described herein may include one or more of a modular assembly, a bifurcated junction, linear needle orientation, a manual slider (e.g., actuation member 112), a needle lock (e.g., tool lock 110), an integrated flush port (e.g., flush port assembly 452), a syringe attachment, and dual strain relief (e.g., strain reliefs 450-1, 450-2). The medical imaging device may include two independent modules: the needle module and the ultrasound module. These two modules may be assembled separately and joined together inside the handle body 443. In various embodiments, one or more of the modules may be interchangeable. For instance, the needle module may be replaced with a module with a different tool, such as another diagnostic and/or therapeutic medical tool. The needle line and the ultrasound line may converge inside a bifurcated junction (e.g., bifurcation junction 664) before feeding into a dual-lumen catheter. The bifurcated junction may dictate the bend radius of the ultrasound line. The needle module (e.g., plunger assembly 640) may be axially aligned with a lumen (e.g., lumen 218-1), such as to reduce the force required to actuate the needle. In other words, the needle module may extend linearly into a first lumen of the dual-lumen catheter.

In various embodiments, one or more features of the medical imaging device may provide for tactile registration. In some embodiments, the extended handle profile and short transition curve may provide more comfortable and substantial grip locations and/or accommodate a wider range of hand sizes. For example, handle assembly 404 may accommodate adult hand sizes ranging from the $5^{th}$ percentile of female hands to the $95^{th}$ percentile of male hands. The displacement gauge 457 (e.g., corresponding to graduated stroke depths of the needle exiting the ramp and the side port) may be readily readable from a variety of viewing angles, such as by partially wrapping around the plunger. In some embodiments, a soft-touch finish on the actuation member 412 may create a contrasting feel to the handle body 443 and/or match the distal handle finish. Some components may include rubberized texture overmolds and/or color accent, such as on the actuation member grip ridge 444. In some embodiments this and other features may provide an improved thumb grip and/or visual travel indication. The handle body may have a smooth/semi-gloss finish in some embodiments. Various embodiments may include a horizontal groove texture on the tool lock 410, such as for an ergonomic detail and/or precision feel. Several embodiments include a textured finish around the tool lock 410 to create tactile contrast, such as for intuitive use. The actuation stop 442 (or hand hilt) and/or grip ridge 444 may provide 360 degree tactile registration. In some embodiments, the actuation stop 442 and/or grip ridge 444 may provide a boundary for hand position and/or hand protection during actuation. Further, the actuation stop 442 and/or grip ridge 444 may provide a non-visual indicator of hand position. Various embodiments may include a soft touch finish and/or slight rubberized texture on a distal portion of the handle body 443.

Several embodiments may include a solid color band that wraps around the handle body to indicate ultrasound zone is exposed when the actuation member 412 is moved distally. In several such embodiments, the band may include a slight texture change and/or an ultrasound icon disposed proximately. In one or more embodiments, an additional part break line on a strain relief connection may allow for individual rotation.

Figure 5A:
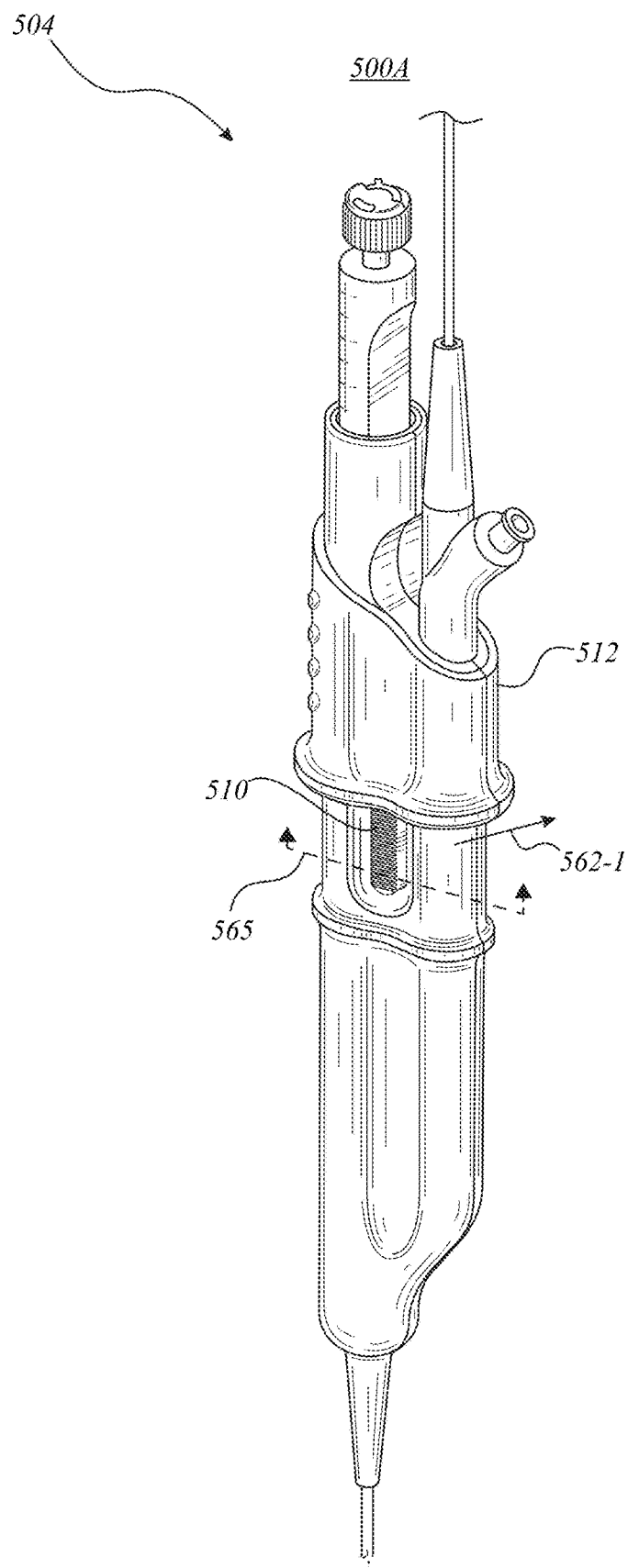
FIGS. 5A-5E illustrate various aspects of an exemplary handle assembly according to one or more embodiments described herein.
Figure 5B:
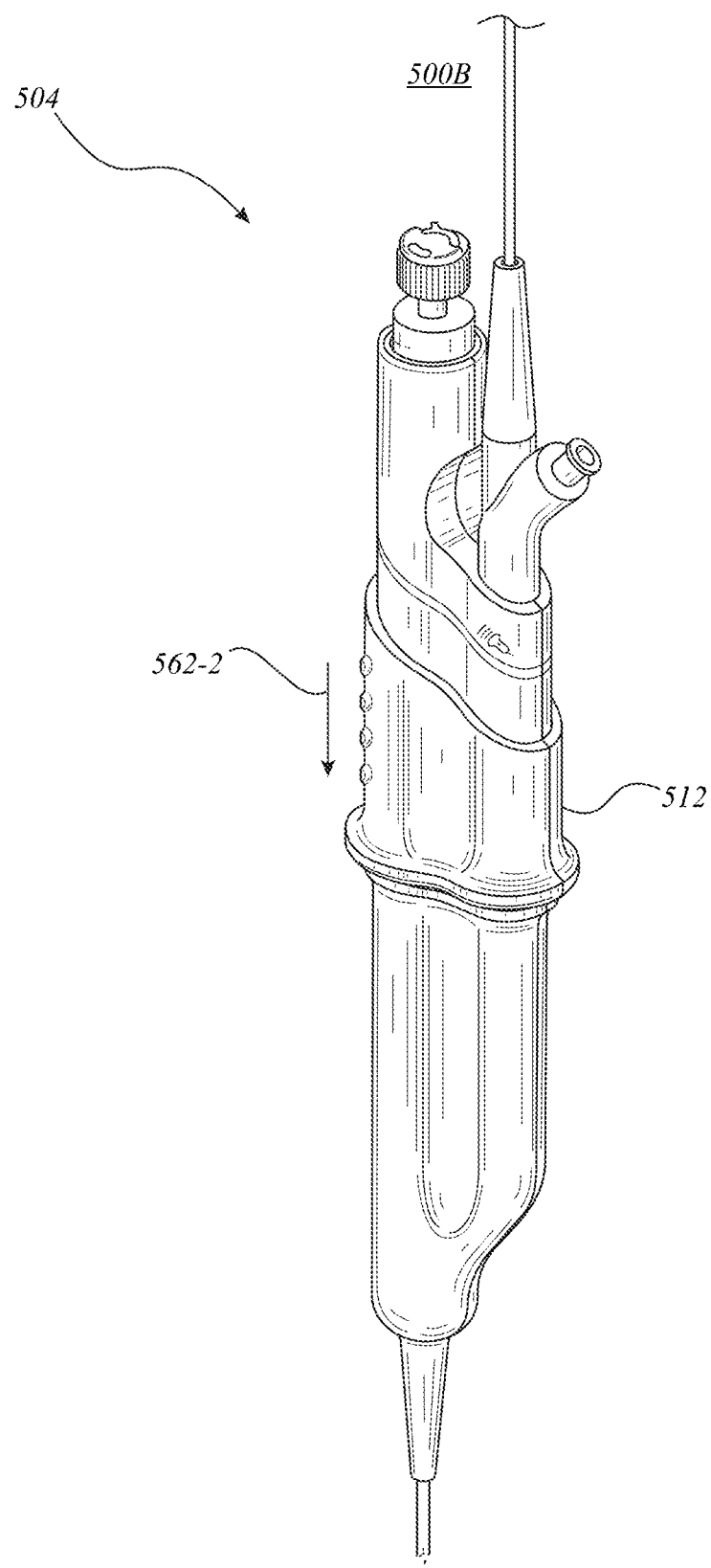
Figure 5C:
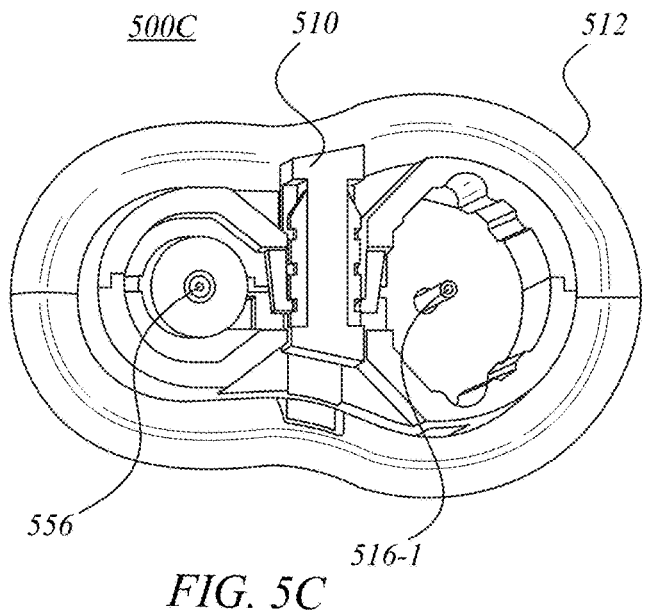
Figure 5D:
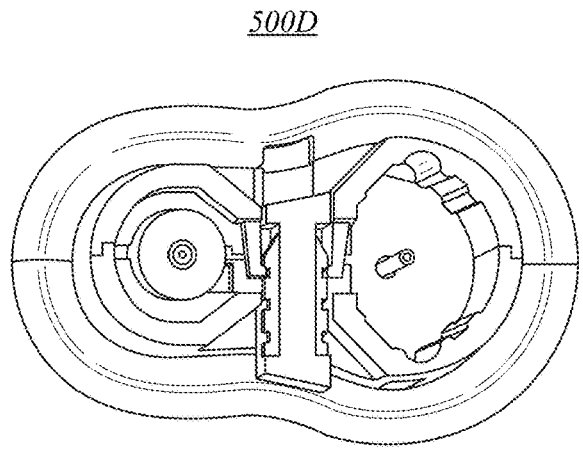
Figure 5E:
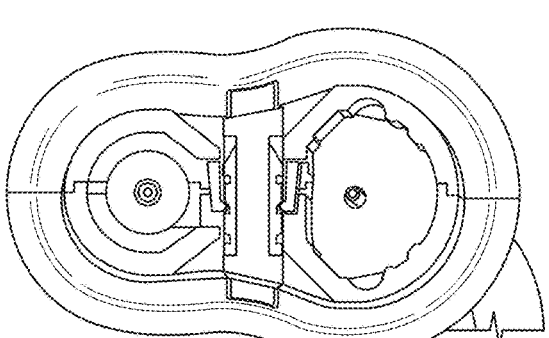

FIGS. 5A-5E illustrate various aspects of an exemplary handle assembly 504 for a medical imaging device according to one or more embodiments described herein. More specifically, FIG. 5A illustrates the handle assembly 504 in an unactuated configuration 500A and FIG. 5B illustrates the handle assembly 504 in an actuated configuration 500B. In various embodiments, actuation member 512 may be moved distally to cause a tool, such as a biopsy needle, to exit the side port of the probe as indicated in the image by the marker. FIGS. 5C-5E illustrate operation of a tool lock 510 of handle assembly 504. In embodiments described herein, components of the handle assembly 504 may facilitate intuitive, ergonomic, and/or single-handed operations to target specific tissues in reliable, intuitive, and unique and advantageous ways. For example, handle assembly 504 may utilize intuitive motions for gripping, locking, unlocking, and actuating to provide for convenient, comfortable, accurate, and fatigue minimizing operation. In many embodiments, one or more components illustrated in FIGS. 5A-5E, or described with respect thereto, may be the same or similar in construction, function, and/or appearance as one or more other components described herein. Embodiments are not limited in this context.

Referring to FIG. 5A, the handle assembly 504 is in unactuated configuration 500A when the distal end of actuation member 512 is positioned proximal of the tool lock 510. In the unactuated configuration 500A, tool lock can be engaged or disengaged. An unlock movement 562-1 may be used to position the tool lock 510 in the middle such that actuation member can move distally over either side of the tool lock 510 in an actuation movement 562-2 to place the handle assembly 504 in an actuated configuration 500B (see e.g., FIG. 5B). The positioning of the tool lock will be discussed in more detail below with reference to cross-sectional line 565. In many embodiments, tool lock 510 may provide a visual indicator of the lock status of the plunger assembly. The ultrasound flush port valve (e.g., flush port assembly) may be integrated into the handle assembly and/or handle body design. In several embodiments, the flush port is positioned and/or positionable away from a grip zone of a user. In various embodiments, the medical imaging device may utilize two syringes (e.g., one for ultrasound flushing and one for needle suction and/or aspiration). In many embodiments, syringes may attach to the medical imaging device with stopcocks Luer-lock fittings, and/or check valves. For example, a check valve may be positioned between the flush port and a syringe connector (e.g., Luer-lock). The handle assembly may include integrated strain relief at both the distal and proximal ends of the handle body (see e.g., strain reliefs 450-1, 450-2). In some embodiments, the distal strain relief (e.g., strain relief 450-1) may be utilized as an additional grip space).

Referring to FIGS. 5C-5E, handle assembly 504 may have positions 500C, 500D, 500E in addition to the unactuated configuration 500A and the actuated configuration 500B. In position 500C, the tool lock 510 may be in a first locked position with actuation member 512 being blocked from moving distally (out of the page). Similarly, in position 500D, the tool lock 510 may be in a second locked position with actuation member 512 being blocked from moving distally (out of the page). In position 500E, tool lock 510 may be in an unlocked position with actuation member 512 not blocked from moving distally (out of the page). This arrangement may allow for actuation of the tool lock 510 from either side of the handle, depending on which side is more accessible to the fingers of the user. Further, as the distal direction is out of the page in FIGS. 5C-5E, it will be appreciated that although the flush port would be visible, it is not illustrated for simplicity.

Figure 6A:
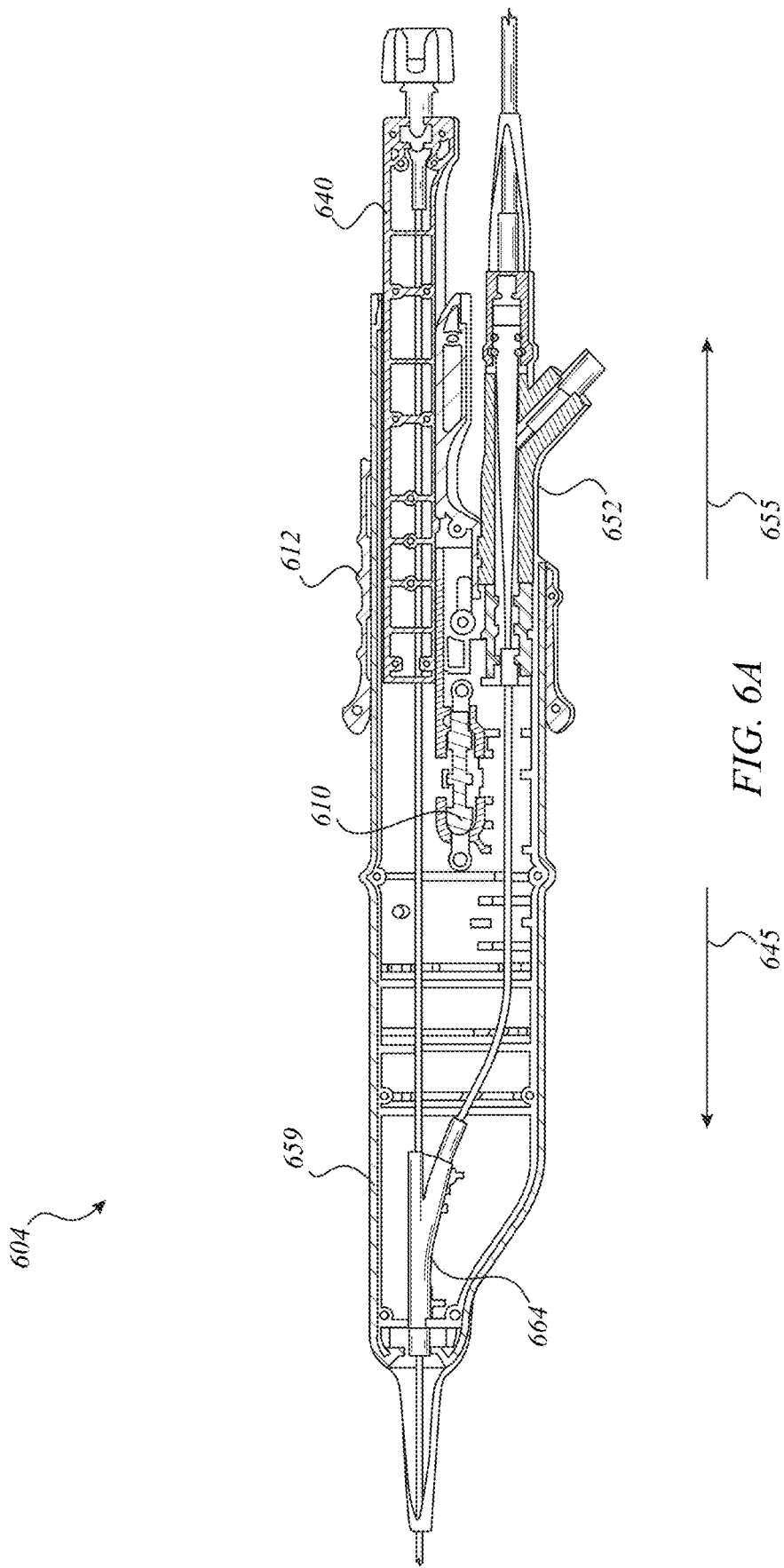
FIGS. 6A and 6B illustrate various internal components of an exemplary handle assembly according to one or more embodiments described herein.
Figure 6B:
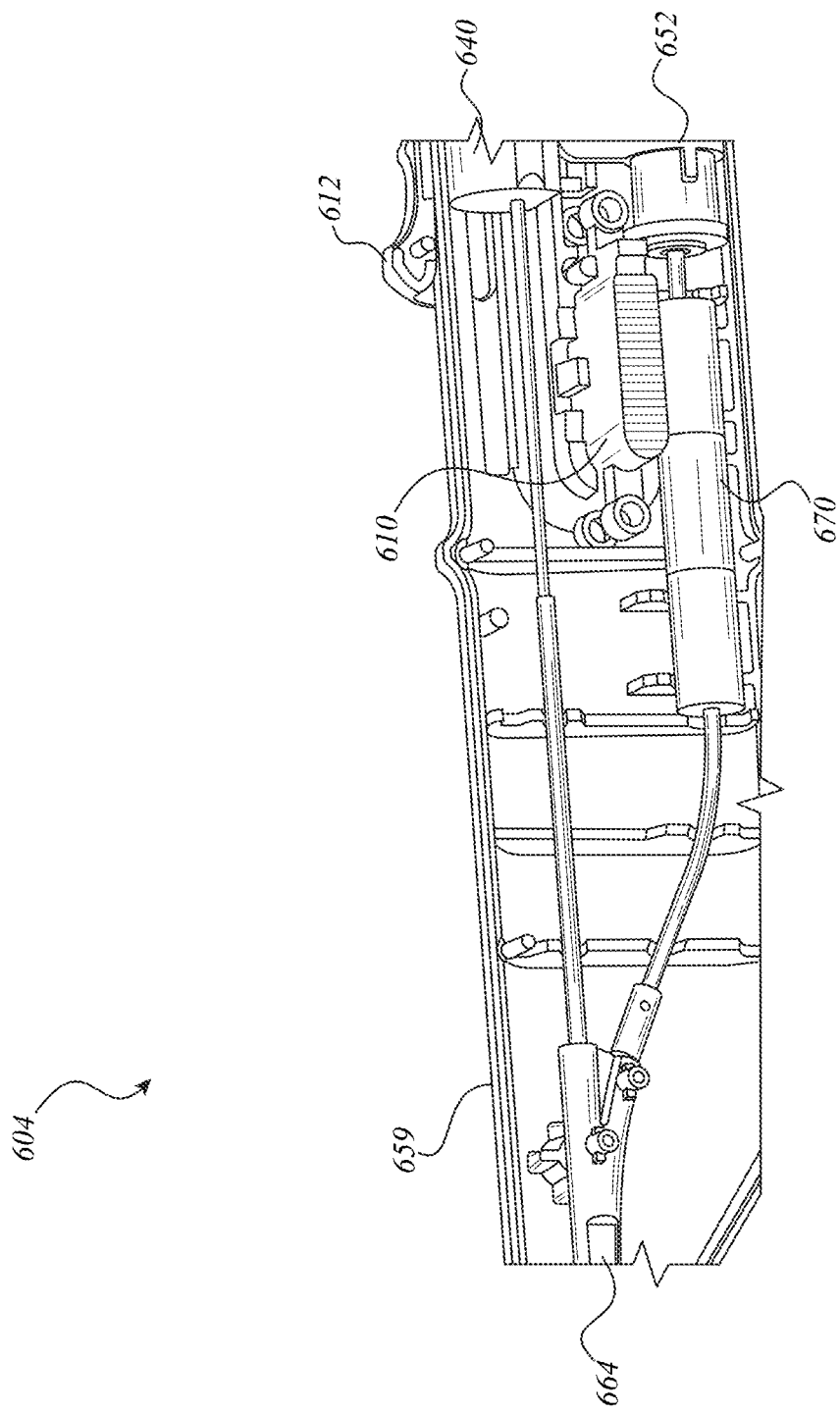

FIGS. 6A and 6B illustrate various internal components of an exemplary handle assembly 604 for a medical imaging device according to one or more embodiments described herein. More specifically, FIG. 6A illustrates a first cross-sectional view of the handle assembly 604 having a distal end 645 and a proximal end 655, and FIG. 6B illustrates a second cross-sectional view of the handle assembly 604. In the illustrated embodiments, handle assembly 604 includes a handle body 659 comprising and/or coupling to a bifurcation joint 664, tool lock 610, actuation member 612, plunger assembly 640, flush port assembly 652, and noise compensators 670. In embodiments described herein, components of the handle assembly 604 may facilitate intuitive, ergonomic, and/or single-handed operations to target specific tissues in reliable, intuitive, unique, and advantageous ways. For example, handle assembly 504 may utilize intuitive motions for gripping, locking, unlocking, and actuating to provide for convenient, comfortable, accurate, and fatigue minimizing operation. In various embodiments, noise compensators 670 may serve to reduce electrical noise in the distal and/or proximal drive cables. For example, noise compensators 670 may be an electronic choke, such as a passive electric component that suppresses high frequency noise in electronic circuits. In some embodiments, one or more of noise compensators 670 may utilize ferrite, such as a ferrite ceramic. In many embodiments, one or more components illustrated in FIGS. 6A and 6B, or described with respect thereto, may be the same or similar in construction, function, and/or appearance as one or more other components described herein. Embodiments are not limited in this context.

Figure 7A:
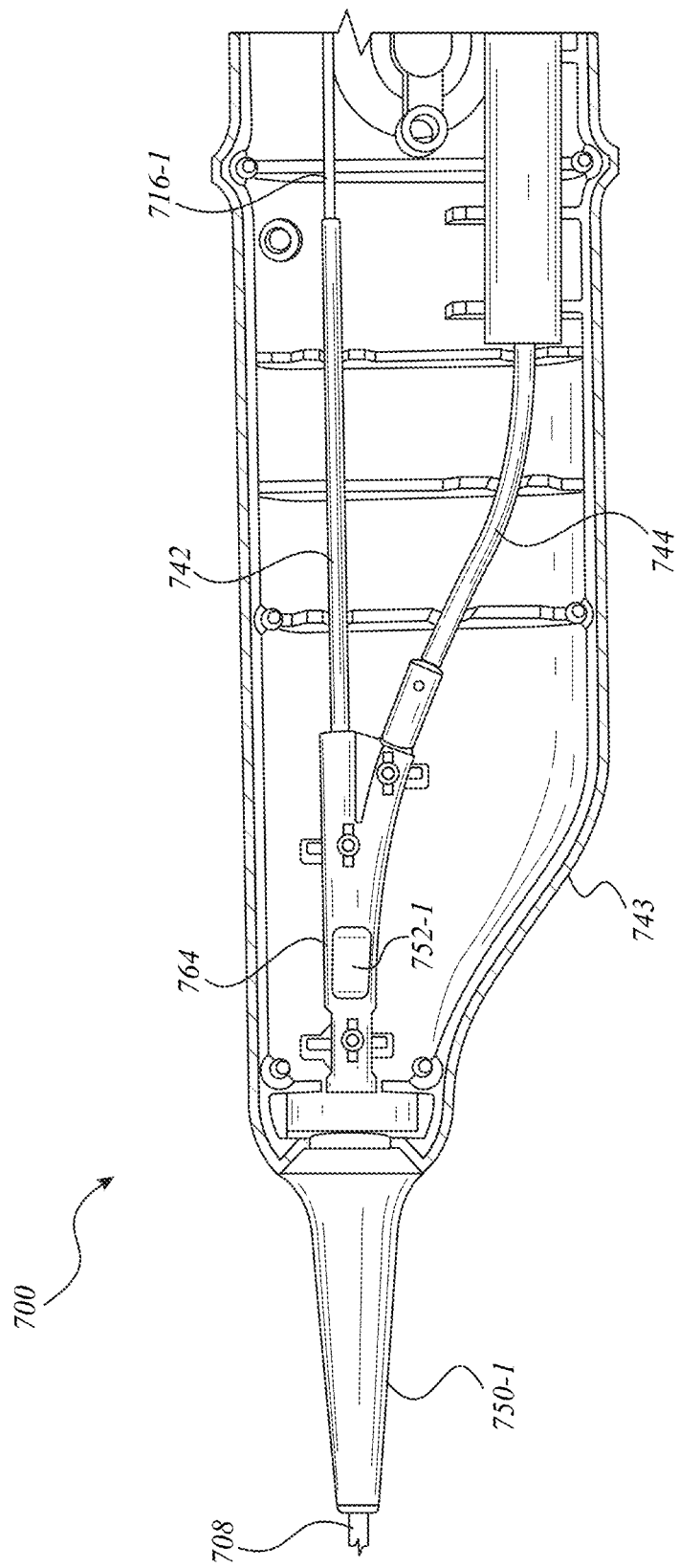
FIGS. 7A-7D illustrate various aspects of an exemplary bifurcation joint for a handle assembly according to one or more embodiments described herein.
Figure 7B:
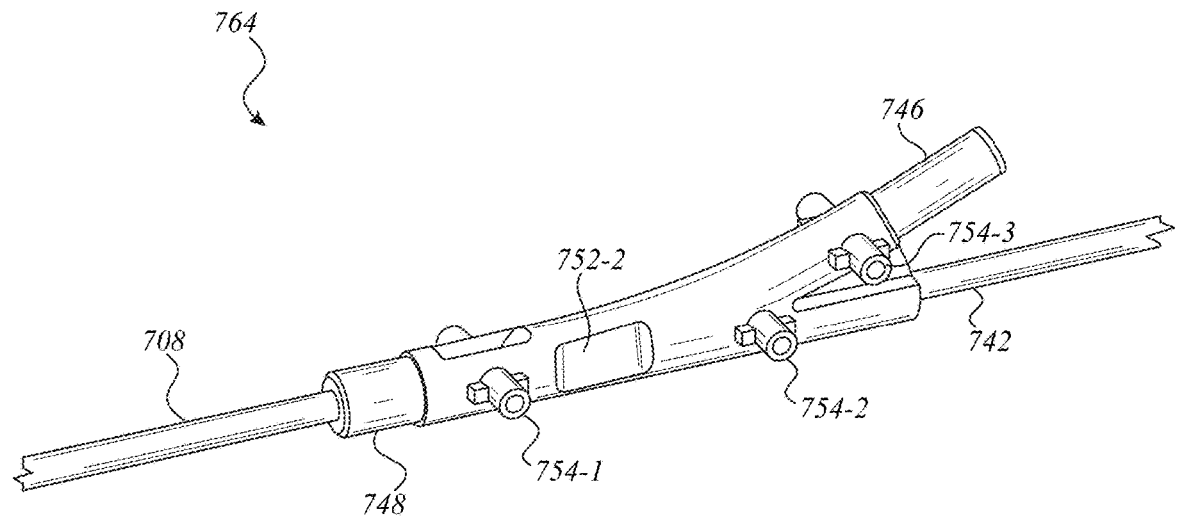
Figure 7C:
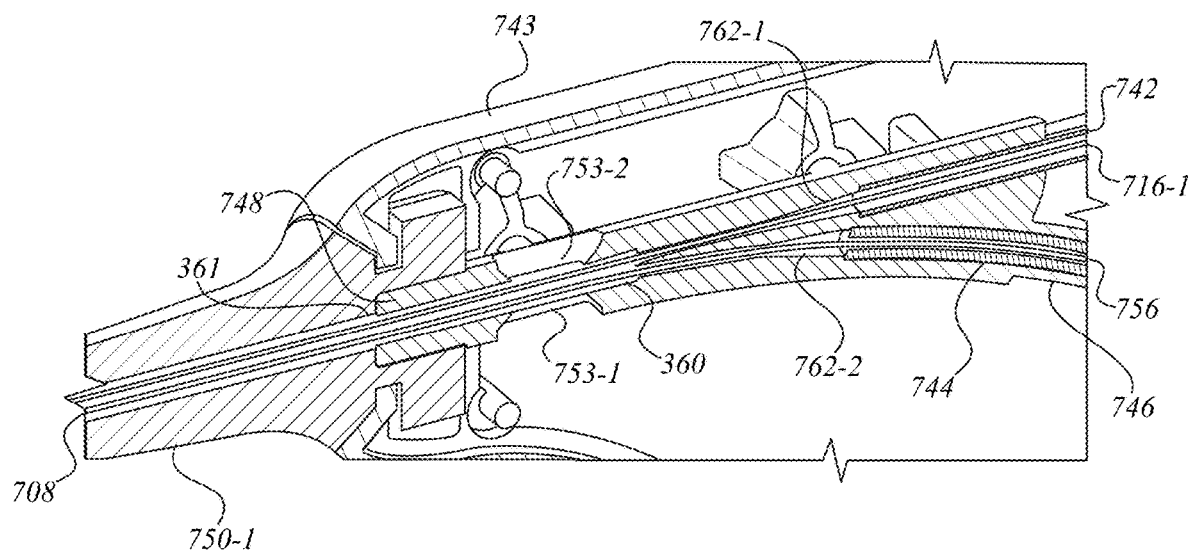
Figure 7D:
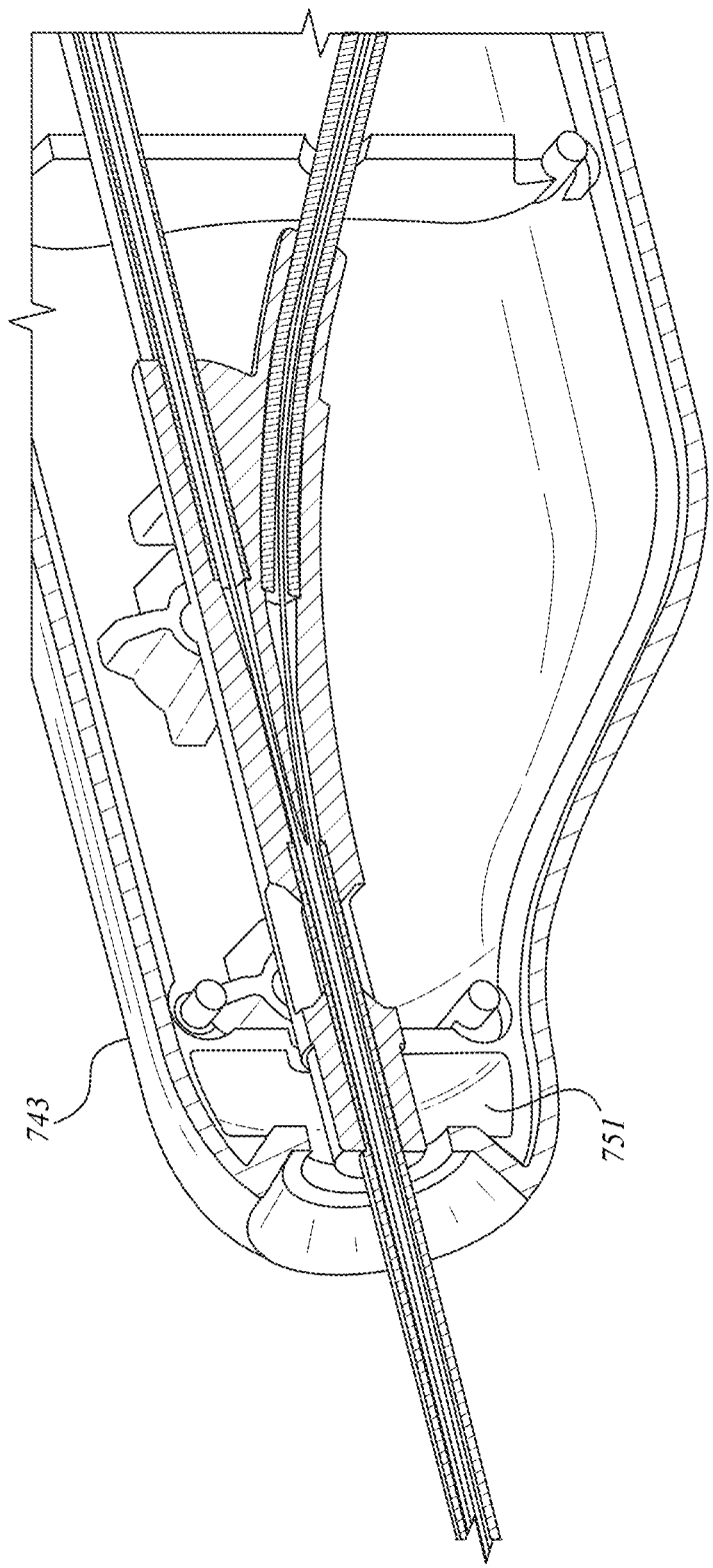

FIGS. 7A-7D illustrate various aspects of an exemplary bifurcation joint 764 for a medical imaging device 700 according to one or more embodiments described herein. More specifically, FIG. 7A illustrates a cross-sectional view of the bifurcation joint 764 in conjunction with a handle body 743. FIG. 7B illustrates the bifurcation joint 764. FIGS. 7C and 7D illustrate cross-sectional views of bifurcation joint 764. In various embodiments, bifurcation joint 764 may connect the needle 716-1 to a first lumen of dual-lumen catheter 708 and a conduit 744 carrying a portion of the distal drive cable 756 to a second lumen of dual-lumen catheter 708. In many embodiments, the bifurcation joint 764 may prevent fluid leaking within the handle body 743 when fluids are passed into the dual-lumen catheter. In embodiments described herein, components of the bifurcation joint 764 may facilitate convenient, reliable, efficient, and leak-proof operation in unique and advantageous ways. For example, the bifurcation joint 764 may reduce or minimize the bend in conduit 744 to limit bend in the drive cable (e.g., ultrasound drive cable). In another example, bifurcation joint 764 includes a needle support 742 to prevent needle 716-1 from bending, such as when it is forced distally by the plunger assembly. In many embodiments, one or more components illustrated in FIGS. 7A-7D, or described with respect thereto, may be the same or similar in construction, function, and/or appearance as one or more other components described herein. Embodiments are not limited in this context.

Referring to FIG. 7A, bifurcation joint 764 may be disposed in handle body 743 and include needle support 742. More generally, bifurcation joint 764 may be the component of the medical imaging device that routes the first and second tools into the first and second lumens of the dual-lumen catheter. In many embodiments, bifurcation joint 764 may align the first and second tools for insertion into the dual-lumen catheter 708 while limiting the amount of bend required. For instance, bifurcation joint 764 may prevent either tool from bending over 20 degrees. In another instance, bifurcation joint 764 may limit bending of a drive cable for a medical imaging device to less than 15 degrees. In many embodiments, the minimum radius of curvature for the drive cable may be 3 inches.

Medical imaging device 700 may also include strain relief 750-1. Strain relief 750-1, or one or more other strain reliefs described herein, may limit bending (e.g., bends over 25 degrees) of the dual-lumen catheter 708 or other portions along the length of tool lumens (e.g., conduit 744). In some embodiments, conduit 744 may comprise a polymer tube, such as a PEEK or Nylon tube. In several embodiments, bifurcation joint 764 supports parallel alignment of the plunger assembly and the flush port assembly in the handle assembly, resulting in an ergonomic and intuitive feel.

Referring to FIG. 7B, the dual-lumen catheter 708 may connect into the bifurcation join 764 at a catheter support 748, conduit 744 may connect into the bifurcation joint 764 at conduit support 749, and needle 116-1 may connect into needle support 742. In many embodiments, needle support 742 may prevent the needle from kinking, paperclipping, bending, and/or breaking. Bifurcation joint 764 may also include mounts 754-1, 754-2, 754-3 (or mounts 754) on both sides and/or indentations 753-1, 753-2 (or indentations 753). In many embodiments, the mounts 754 may be used to attach the bifurcation joint 764 to handle body 743. As previously mentioned, in one or more embodiments, handle body 743 may connect one or more components of a medical imaging device, such as by serving as one or more of a mounting point, enclosure, structure, and the like. Additionally, or alternatively, bifurcation joint 764 may include one or more view windows 752-1, 752-2 (or view windows 752). In various embodiments, the view windows 752 may allow visual verification the contents of the lumens as they pass through the bifurcation joint.

FIG. 7C includes a cross-sectional view of the bifurcation joint 764. As shown in FIG. 7C, the layer of braid 360 and the tubular member (not labeled) begin on the proximal side of the indentations 752 and the layer of reflow 361 on the dual-lumen catheter begins at the distal end of the bifurcation joint 764. Additionally, or alternatively, conduit 744 ends between the view windows 752 and the conduit support 746. The needle support 742 ends proximate to the end of conduit 744. In several embodiments, immediately distal of the needle support 742, the first lumen of the bifurcation joint includes a junction taper 762-1. In various embodiments, immediately distal of the conduit 744, the second lumen of bifurcation joint includes a junction taper 762-2. In some embodiments, the junction tapers 762 facilitate one or more of retaining the conduit/needle support connected, limiting a bending radius, and improving fluid flow (such as preventing leaks or reducing turbulent flow). In medical imaging device 700, needle 716-1 may pass through the first lumen of bifurcation joint 764 and distal drive cable 756 may pass through the second lumen of bifurcation joint 764. FIG. 7D illustrates handle body 743 with strain relief 750-1 removed, leaving strain relief pocket 751.

Figure 8A:
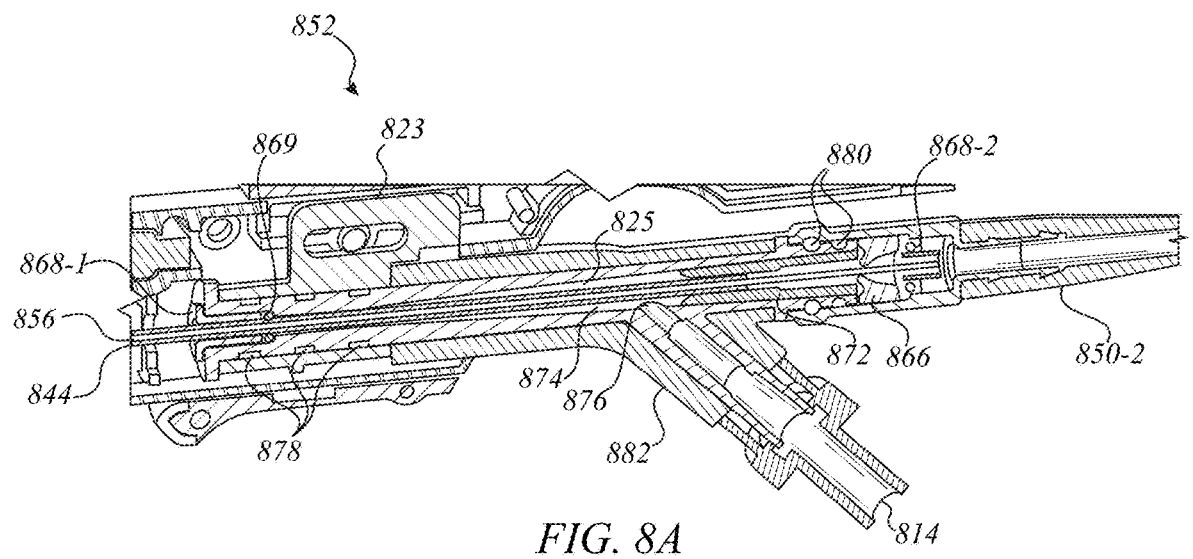
FIGS. 8A-8J illustrate various aspects of an exemplary flush port assembly for a handle assembly according to one or more embodiments described herein.
Figure 8B:
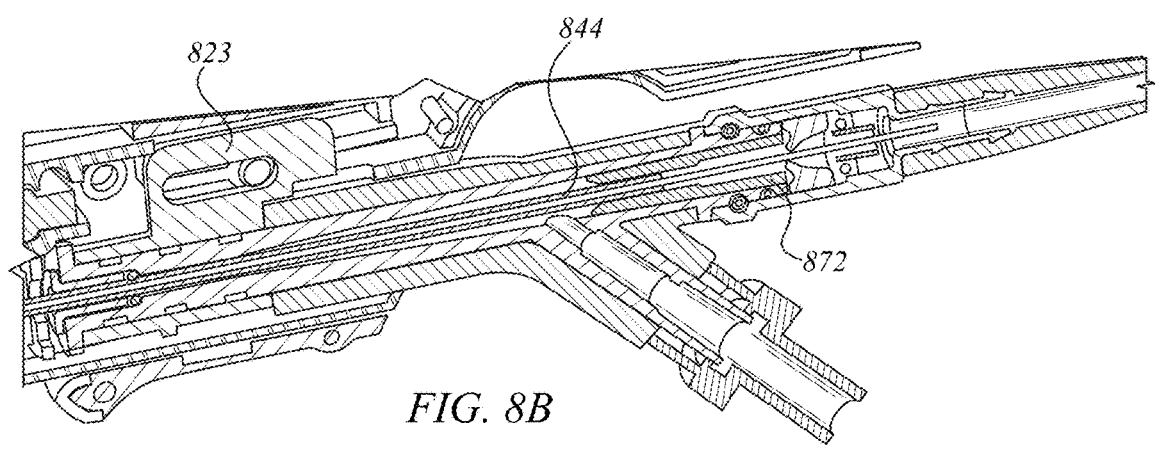
Figure 8C:
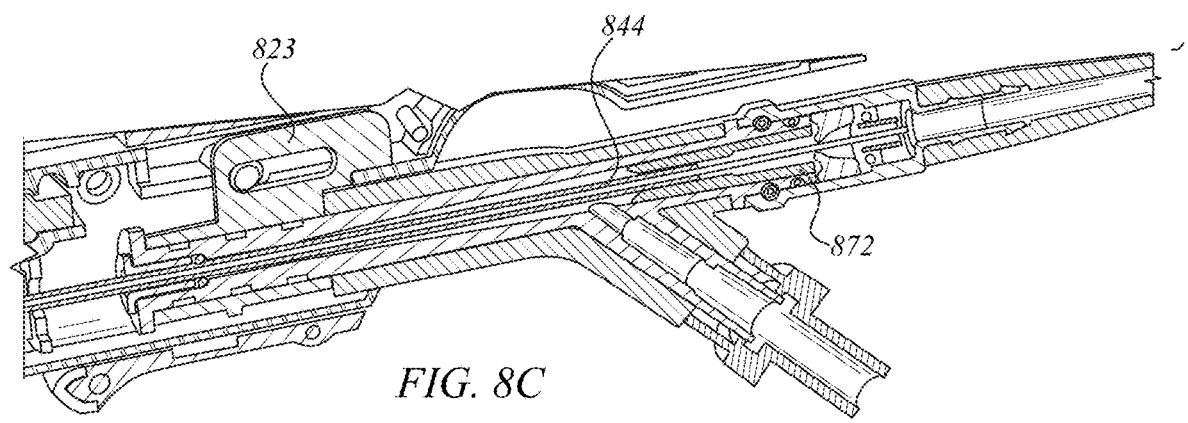
Figure 8D:
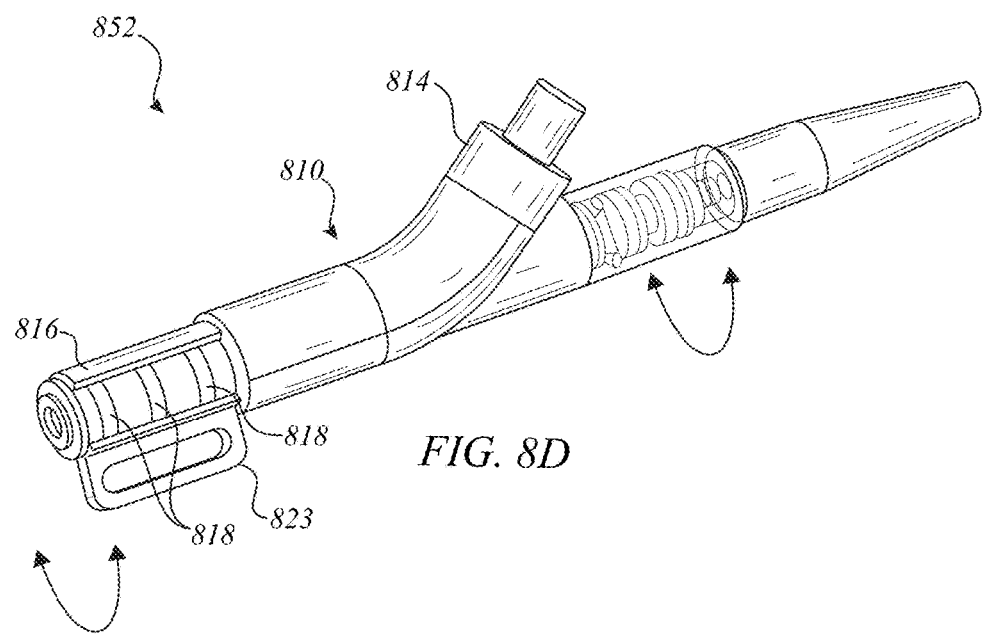
Figure 8E:
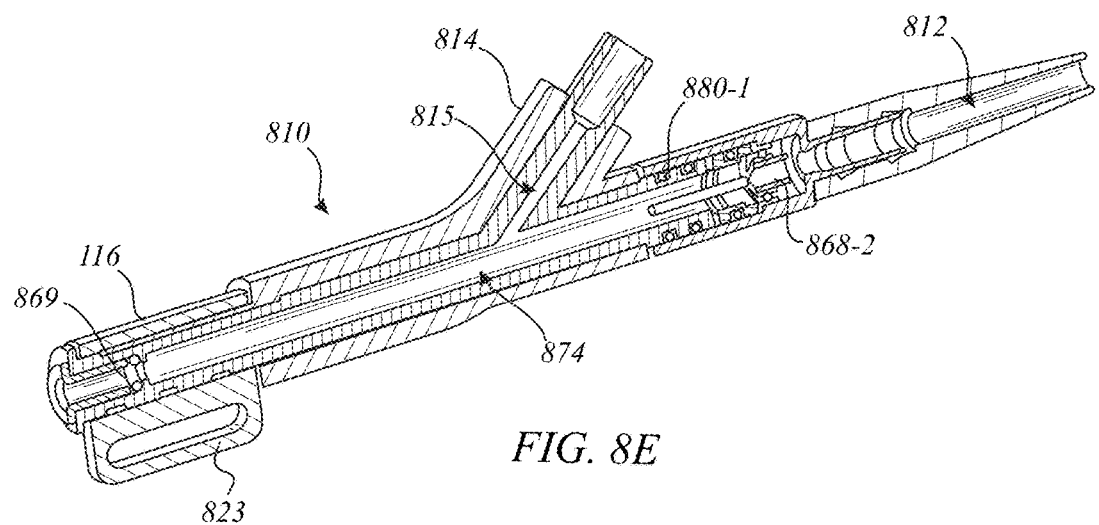
Figure 8F:
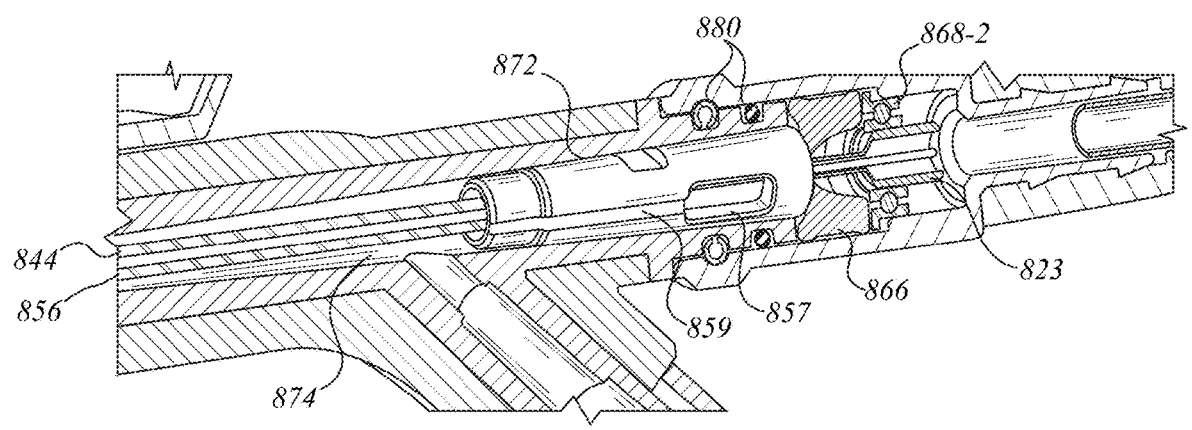
Figure 8G:
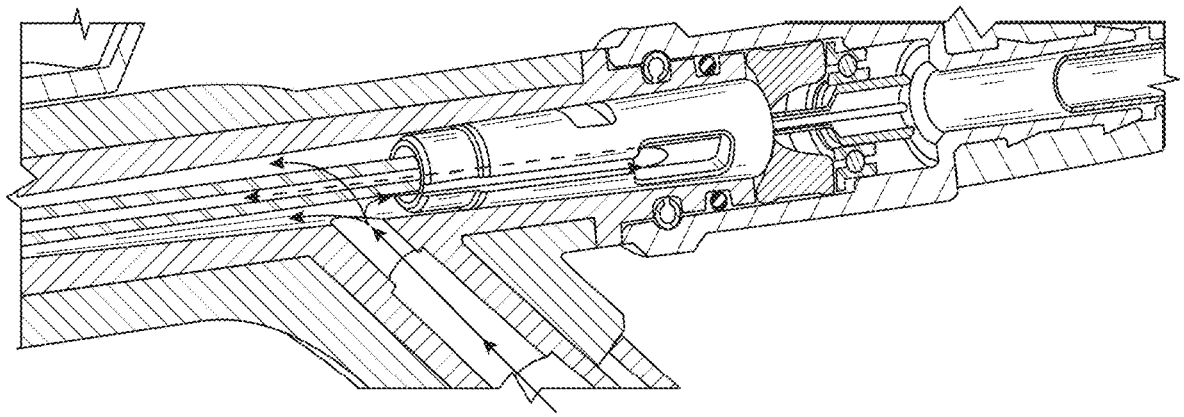
Figure 8H:
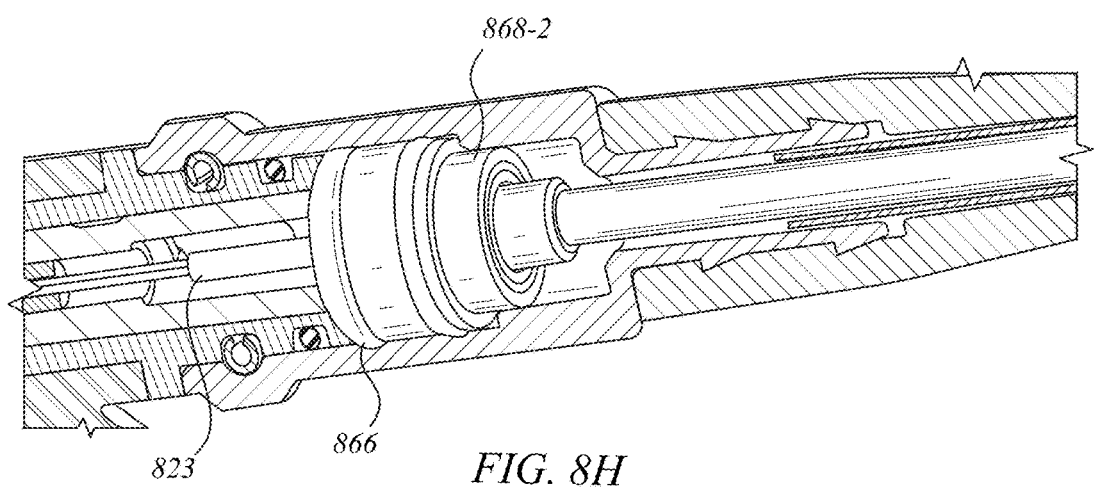
Figure 8I:
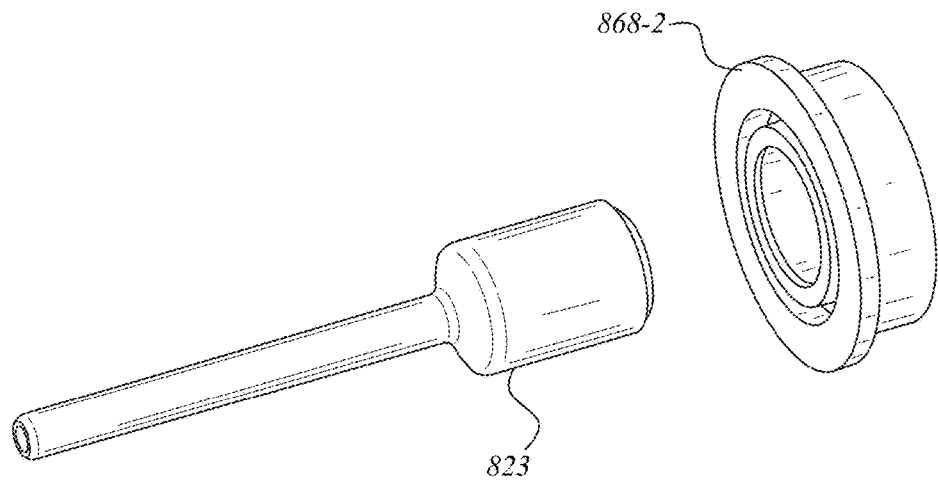
Figure 8J:
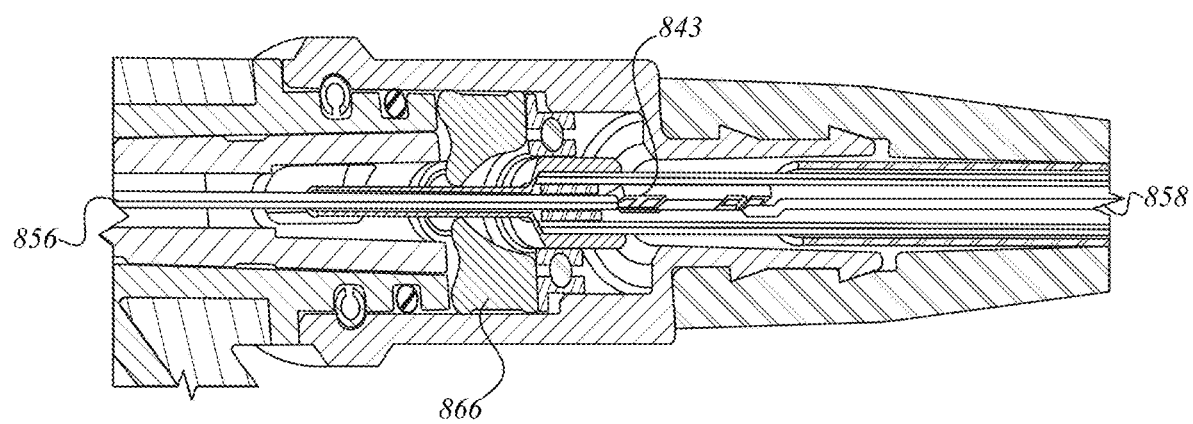

FIGS. 8A-8J illustrate various aspects of an exemplary flush port assembly 852 for a medical imaging device according to one or more embodiments described herein. More specifically, FIG. 8A illustrates a cross-sectional view of the flush port assembly 852. FIGS. 8B and 8C illustrate axial displacement of flush port assembly 852 in distal and proximal directions, respectively. FIG. 8D illustrates axial rotation of flush port assembly 852. FIG. 8E illustrates various aspects of the flush port assembly 852. FIG. 8F illustrates various components of flush port assembly 852. FIG. 8G illustrates a flow path 861 from flush port 814 into conduit 844. FIGS. 8H and 8I illustrate various aspects of the flush port assembly 852 including a stabilizer 823 and a bearing 868-2. FIG. 8J illustrates an impedance compensator 843 disposed between a distal drive cable 856 and a proximal drive cable. In embodiments described herein, components of the flush port assembly 852 may facilitate convenient, reliable, efficient, and leak-proof operation in unique and advantageous ways. For example, the flush port assembly 852 may rotate independently of the proximal and distal drive cables 856, 858 while maintaining a seal with conduit 844 that facilitates introduction of fluid into the conduit 844 around the distal drive cable 856. In another example, impedance compensator 843 matches impedance between the distal and proximal drive cables 856, 858. In many embodiments, one or more components illustrated in FIGS. 8A-8J, or described with respect thereto, may be the same or similar in construction, function, and/or appearance as one or more other components described herein. Embodiments are not limited in this context.

Referring to FIG. 8A, flush port assembly 852 may include bearings 868-1, 868-2, seal 869, slide mount 823, proximal surface features 880, strain relief 850-2, lip seal 866, port member 872, flush port 814, port interface 882, flow junction 876, flow chamber 874 with taper 825, distal surface features 878, a proximal portion of conduit 844, a portion of the distal drive cable 856 and a portion of the proximal drive cable 858. One or more components described herein (e.g., port interface 882) may be formed via a molding, extrusion, and/or machining procedure (e.g., overmolding, injection molding, vacuum molding, cold extrusion, lathe, and the like).

As previously mentioned, the flush port assembly 852 may be able to be adjusted in the proximal and distal directions. Accordingly, FIG. 8B illustrates the port assembly 852 including slide mount 823, conduit 844, and port member 872 in the distal most position and FIG. 8C illustrates the port assembly 852 including slide mount 823, conduit 844, and port member 872 in the proximal most position. In many embodiments, conduit 844 may be supported by a slide within port member 872 as it is proximally and distally moved with respect to the longitudinal axis of the device. The slide mount 823 may couple with a peg or mounting point on the handle body. In various embodiments, adjustment along slide mount 823 may be utilized to calibrate the location of the imaging transducer with respect to the imaging window, such as during manufacture. In some embodiments, the end user may be able to adjust along the slide mount 823.

Referring to FIGS. 8D-8E, in one embodiment, a flush port assembly 852 of the present disclosure may include a housing 810 defining a flow chamber 874. An ultrasound port 812 (e.g., first port) may be formed within or otherwise extend through a proximal portion of the housing 810. In various embodiments, the ultrasound port 812 may be coextensive (e.g., substantially aligned with, etc.) with the flow chamber 874. A flush port 814 (e.g., second port) defining a fluid channel 115 therethrough may be disposed along (e.g., attached to, integrally formed with, etc.) a middle portion of the housing 810. A fitting 816 may be disposed around a distal portion of the housing 810. In various embodiments, the housing 810 may be configured to rotate 360° (e.g., move axially) within the fitting 816 to alter a position of the flush port 814 relative to a longitudinal axis of the flush port assembly 852 (e.g., move proximally or distally) and/or rotate (e.g., alter an axial position of) a radial ultrasound probe extending through the housing 810 (as discussed below). An outer surface of the distal portion of the housing may include distal surface features 818 configured to frictionally engage a corresponding inner surface of the fitting 816. By way of non-limiting example, the surface feature may include a rubber seal or O-ring configured to maintain or lock an axial position of the housing 810 relative to the fitting 816 until a threshold level of rotational force is exerted on the housing 810 (e.g., a sufficient amount of force exerted by a physician's hand). In various embodiments, an outer surface of the housing 810 and/or flush port 814 may include a non-slip surface (e.g., over-molded or coated with rubber, etc.) to provide a physician with sufficient grip to manipulate the housing 810, e.g., when wearing wet gloves, etc. Slide mount 823 (e.g., an arm or projection) may extend from an outer surface of the fitting 816 to anchor or lock the housing of the probe assembly within a handle body (e.g., handle body 743) of a medical imaging device with radial ultrasound and needle biopsy capability.

In one embodiment, a first seal 869 (e.g., O-ring, etc.) may be disposed within a distal portion of the flow chamber 874 (e.g., proximal to a distal opening of the housing 810) and a second seal 124 may be disposed within a proximal portion of the flow chamber 874 (e.g., distal to a proximal opening of the housing 810). The first and second seals 869, 880-1 may be configured to prevent fluid introduced (e.g., flushed) through the fluid channel 815 of the flush port 814 from exiting the flow chamber 874 (e.g., flowing/leaking distally beyond the first seal 869 or proximally beyond the second seal 124). A bearing 126 may be disposed within the proximal portion of the flow chamber 874 proximal to the second seal 124. In various embodiments, the housing 810 and ultrasound port 812 may be configured to receive a proximal portion of a tool (e.g., a radial ultrasound probe) therethrough. The bearing 126 may be configured to receive an outer surface of the radial ultrasound probe 130 to support/facilitate rotation of the radial ultrasound probe within the housing 810.

FIGS. 8F and 8G illustrate various components of the flush port assembly 852, such as those associated with fluid flow. The flush port assembly 852 of FIG. 8F includes conduit 844, port member 872, proximal surface features 880, bearing 868-2, stabilizer 823, lip seal 866, flow port 857, flow channel 859, flow chamber 874, distal drive cable 856, and conduit 844. FIG. 8G illustrates a flow path 861 of fluid introduced via the flush port 814. Accordingly, the flow path 861 may enter via the flush port 814, fill flow chamber 874, follow flow channel 859 of port member 842, enter flow port 857 of port member 872, and proceed into the conduit 844 around the distal drive cable 856. In various embodiments, the lumens and/or flow components described herein may be designed to handle at least 43 pounds per square inch. Such pressure rating may vary as dictated by design and/or performance requirements.

FIG. 8H illustrates stabilizer 823, lip seal 866, and bearing 868-2 and FIG. 8I illustrates stabilizer 823 and bearing 868-2. In various embodiments, the stabilizer 823 may extend through one or more of the bearing 868-2 and lip seal 866. The drive cable may extend through the stabilizer 823. In many embodiments, the stabilizer may prevent loss of stability during rotation of the drive cable.

Referring to FIG. 8J, proximal of the stabilizer 823, an impedance compensator 843 may connect distal drive cable 856 and proximal drive cable 858. In several embodiments, the proximal and distal drive cable along with the imaging transducer may rotate at up to 2000 or more revolutions per minute (rpm). For instance, the imaging transducer (and drive cables) may rotate at 1800 rpm. In various embodiments, impedance compensator 843 may adapt for a diameter change between the distal and proximal drive cables 856, 858. In many embodiments, the impedance compensator spins along with the distal and proximal drive cables 856, 858. In one or more embodiments, the impedance compensator 843 comprises a printed circuit board (PCB). In many embodiments, the lumen of the distal drive cable 856 is a uniform size to prevent kinking or winding up of the distal drive cable. In some embodiments, the diameter change between the proximal and distal drive cables prevents signal degradation. For example, if the proximal drive cable was as small as the distal drive cable, unacceptable levels of signal degradation may occur. In some embodiments, making the proximal drive cable 856 have a larger diameter than the distal drive cable 858, reduced electromagnetic emissions (e.g., noise) can be achieved, such as via lower signal voltages. In several embodiments, one or more of the stabilizer 823, and the impedance compensator 843 may be filled with epoxy, such as to prevent fluid from leaking around the distal drive cable 856 and into the impedance compensator 843 via the stabilizer 823.

FIG. 9 illustrates various internal components of an exemplary imaging controller 990 according to one or more embodiments described herein. Ultrasound controller 990 may include logic circuitry 992, memory 994, input/output (I/O) 996, and user interface 998. As previously mentioned, imaging controller 990 may couple with an imaging transducer 916-2 via a proximal drive cable 958 connected between the hub assembly 906 and an impedance compensator 943, and a distal drive cable 956 connected between the impedance compensator 943 and the imaging transducer 916-2. In embodiments described herein, components of the imaging control 990 may facilitate intuitive, accessible, dynamic monitoring and control over imaging transducer 916-2 in reliable, valuable, unique, and advantageous ways. For example, imaging controller 990 may control one or more of the calibration, frequency, resolution, translation, interpretation, integration, analysis, and/or display of images generated by one or more medical imaging devices described herein. In one or more embodiments, imaging controller 990 may utilize one or more of historical, contextual, user input, and sensor data to control aspects of the medical imaging device. For example, historical data may include sensor and/or imaging data from previous procedures. In some such embodiments, the historical data may be annotated based on user input. In many embodiments, one or more components illustrated in FIG. 9, or described with respect thereto, may be the same or similar in construction, function, and/or appearance as one or more other components described herein. Embodiments are not limited in this context.

In various embodiments, proximal and distal drive cable 958, 956 may comprise multiple conductors. In some embodiments, the drive cables may be coaxial cables. In various embodiment, the drive cables may provide one or more of power, torque, communication between the imaging transducer and the imaging controller.

One or more of the components, devices, and/or techniques described herein may be used as part of a system to facilitate the performance of medical procedures (e.g., peripheral lung nodule biopsy) in a safe, efficient, and reliable manner. In many embodiments, the novel system may include one or more medical devices capable of locating a patient-specific anatomy, positioning a flexible elongate member for access to the patient-specific anatomy, and accessing the patient-specific anatomy in a safe, accurate, and reliable manner. In these and other ways, components/techniques described here may improve patient care, increase user experience, decrease learning curve, improve success rates, and/or decrease adverse outcomes via realization of a more efficient and better functioning medical device with advantageous features. In many embodiments, one or more of the advantageous features may result in several technical effects and advantages over conventional devices and technology, including increased capabilities and improved adaptability. In various embodiments, one or more of the aspects, techniques, and/or components described herein may be implemented in a practical application via one or more computing devices, and thereby provide additional and useful functionality to the one or more computing devices, resulting in more capable, better functioning, and improved computing devices. Further, one or more of the aspects, techniques, and/or components described herein may be utilized to improve one or more technical fields including imaging, endoscopy, cannulation, diagnosis, treatment, imaging, robotics, embedded systems and/or control systems.

In several embodiments, components described herein may provide specific and particular manners to render, interpret, transform, analyze, monitor, and/or characterize images generated by the medical imaging device, such as via imaging transducer 316-2 (see e.g., FIG. 3B). In several such embodiments, the specific and particular manners may include, for instance, controlling, monitoring, and/or interfacing with one or more of a transducer, a joint, a working channel, and a user interface to facilitate one or more endoscopy procedures. In one example, the specific and particular manner may simplify pulmonary procedures to facilitate medical professional to quickly learn to safely and reliably biopsy a target nodule.

In many embodiments, one or more of the components described herein may be implemented as a set of rules that improve computer-related technology by allowing a function not previously performable by a computer that facilitates an improved technological result to be achieved. In many embodiments, the function allowed is associated with medical imaging devices and/or procedures. For example, the function allowed may include creating a combined image comprising a characteristic of a wall of a body lumen and a characteristic external to the wall of the body lumen based on the first image generated via a first imaging mode and a second image generated via a second imaging mode. In some embodiments, the function allowed may include positioning a transducer within a focal region of another transducer with one or more joints, such as to facilitate image generation with the transducer. In various embodiments, the function allowed may include utilizing one or more joints to locate and/or access objectives of a cannulation procedure.

Figure 10:
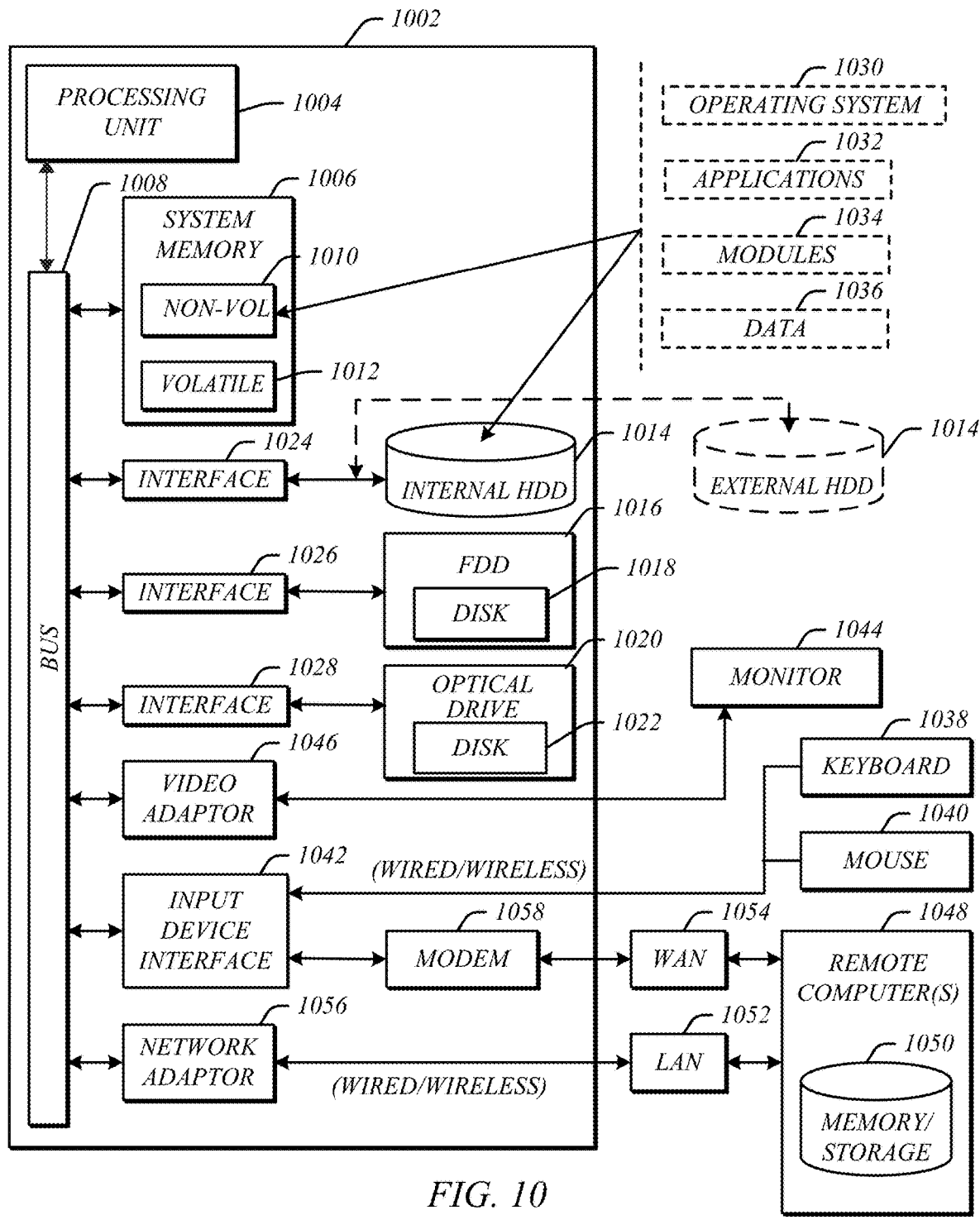
FIG. 10 illustrates an embodiment of a computing architecture according to one or more embodiments described herein.

FIG. 10 illustrates an embodiment of an exemplary computing architecture 1000 that may be suitable for implementing various embodiments as previously described. In various embodiments, the computing architecture 1000 may comprise or be implemented as part of an electronic device and/or medical device. In some embodiments, the computing architecture 1000 may be representative, for example, of one or more components described herein. In some embodiments, computing architecture 1000 may be representative, for example, of a computing device that implements or utilizes one or more portions of components and/or techniques described herein, such as imaging controller 990, logic circuitry 992, memory, 994, I/O 996, and/or user interface 998. The embodiments are not limited in this context.

As used in various embodiments herein, the terms "system" and "component" and "module" can refer to a computer-related entity, either hardware, a combination of hardware and software, software, or software in execution, examples of which are provided by the exemplary computing architecture 1000. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a controller 106 and the controller 106 can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1000 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1000.

As shown in FIG. 10, the computing architecture 1000 comprises a processing unit 1004, a system memory 1006 and a system bus 1008. The processing unit 1004 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1004.

The system bus 1008 provides an interface for system components including, but not limited to, the system memory 1006 to the processing unit 1004. The system bus 1008 can be any of several types of bus structure that may further interconnect to a memory bus (with or without a memory controller), a peripheral bus, and a local bus using any of a variety of commercially available bus architectures. Interface adapters may connect to the system bus 1008 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1006 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 10, the system memory 1006 can include non-volatile memory 1010 and/or volatile memory 1012. In some embodiments, system memory 1006 may include main memory. A basic input/output system (BIOS) can be stored in the non-volatile memory 1010.

The computer 1002 may include various types of computer-readable storage media in the form of one or more lower speed memory units, including an internal (or external) hard disk drive (HDD) 1014, a magnetic floppy disk drive (FDD) 1016 to read from or write to a removable magnetic disk 1018, and an optical disk drive 1020 to read from or write to a removable optical disk 1022 (e.g., a CD-ROM or DVD). The HDD 1014, FDD 1016 and optical disk drive 1020 can be connected to the system bus 1008 by an HDD interface 1024, an FDD interface 1026 and an optical drive interface 1028, respectively. The HDD interface 1024 for external drive implementations can include at least one or both of Universal Serial Bus (USB) and Institute of Electrical and Electronics Engineers (IEEE) 994 interface technologies. In various embodiments, these types of memory may not be included in main memory or system memory.

The drives and associated computer-readable media provide volatile and/or nonvolatile storage of data, data structures, computer-executable instructions, and so forth. For example, a number of program modules can be stored in the drives and memory units 1010, 1012, including an operating system 1030, one or more application programs 1032, other program modules 1034, and program data 1036. In one embodiment, the one or more application programs 1032, other program modules 1034, and program data 1036 can include or implement, for example, the various techniques, applications, and/or components described herein.

A user can enter commands and information into the computer 1002 through one or more wire/wireless input devices, for example, a keyboard 1038 and a pointing device, such as a mouse 1040. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1004 through an input device interface 1042 that is coupled to the system bus 1008 but can be connected by other interfaces such as a parallel port, IEEE 994 serial port, a game port, a USB port, an IR interface, and so forth.

A monitor 1044 or other type of display device is also connected to the system bus 1008 via an interface, such as a video adaptor 1046. The monitor 1044 may be internal or external to the computer 1002. In addition to the monitor 1044, a computer typically includes other peripheral output devices, such as speakers, printers, and so forth.

The computer 1002 may operate in a networked environment using logical connections via wire and/or wireless communications to one or more remote computers, such as a remote computer 1048. In various embodiments, one or more interactions described herein may occur via the networked environment. The remote computer 1048 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1050 is illustrated. The logical connections depicted include wire/wireless connectivity to a local area network (LAN) 1052 and/or larger networks, for example, a wide area network (WAN) 1054. Such LAN and WAN networking environments are commonplace in offices and companies, and facilitate enterprise-wide computer networks, such as intranets, all of which may connect to a global communications network, for example, the Internet.

When used in a LAN networking environment, the computer 1002 is connected to the LAN 1052 through a wire and/or wireless communication network interface or adaptor 1056. The adaptor 1056 can facilitate wire and/or wireless communications to the LAN 1052, which may also include a wireless access point disposed thereon for communicating with the wireless functionality of the adaptor 1056.

When used in a WAN networking environment, the computer 1002 can include a modem 1058, or is connected to a communications server on the WAN 1054 or has other means for establishing communications over the WAN 1054, such as by way of the Internet. The modem 1058, which can be internal or external and a wire and/or wireless device, connects to the system bus 1008 via the input device interface 1042. In a networked environment, program modules depicted relative to the computer 1002, or portions thereof, can be stored in the remote memory/storage device 1050. It will be appreciated that the network connections shown are exemplary and other means of establishing a communications link between the computers can be used.

The computer 1002 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor (e.g., logic circuitry), which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine (e.g., logic circuitry), may cause the machine to perform a method and/or operation in accordance with the embodiments. Such a machine may include, for example, any suitable processing platform, computing platform, computing device, processing device, computing system, processing system, computer, processor, logic circuitry, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Figure 11A:
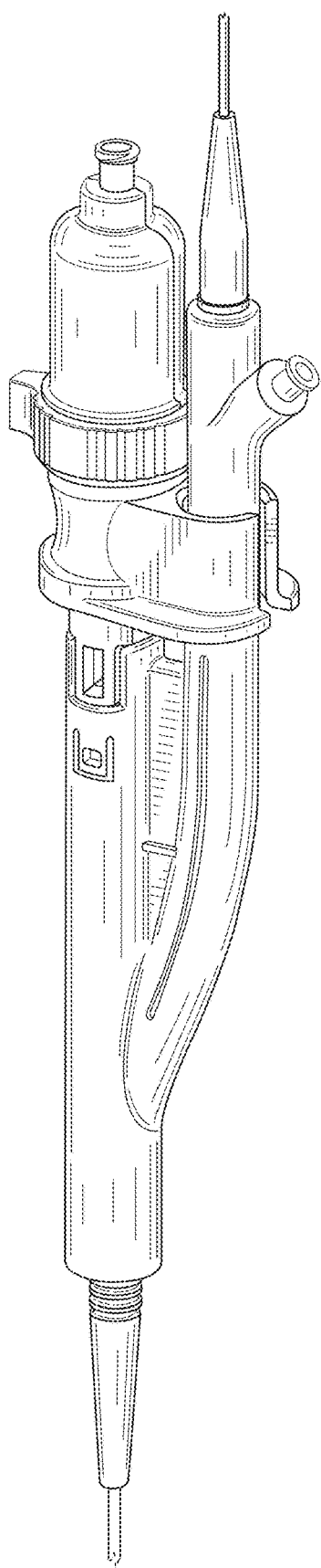
Figure 11B:
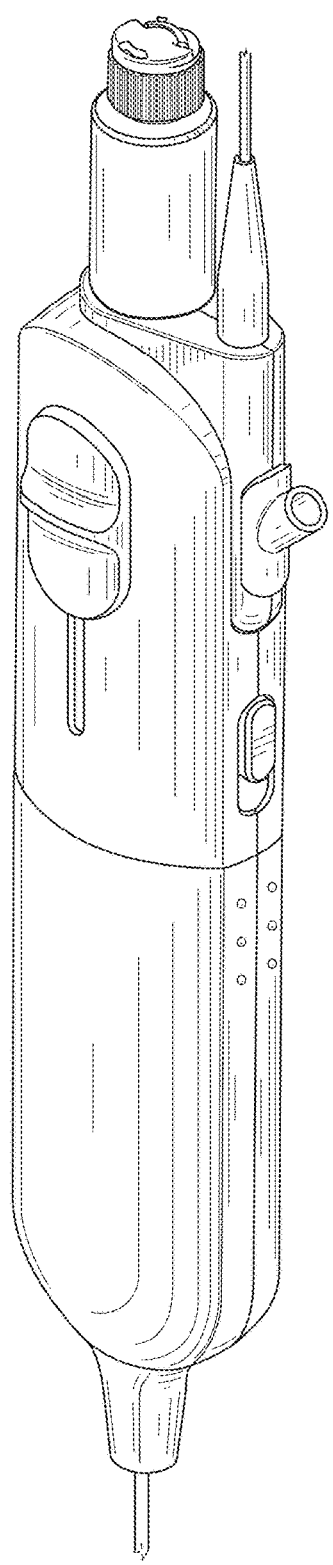
Figure 11C:
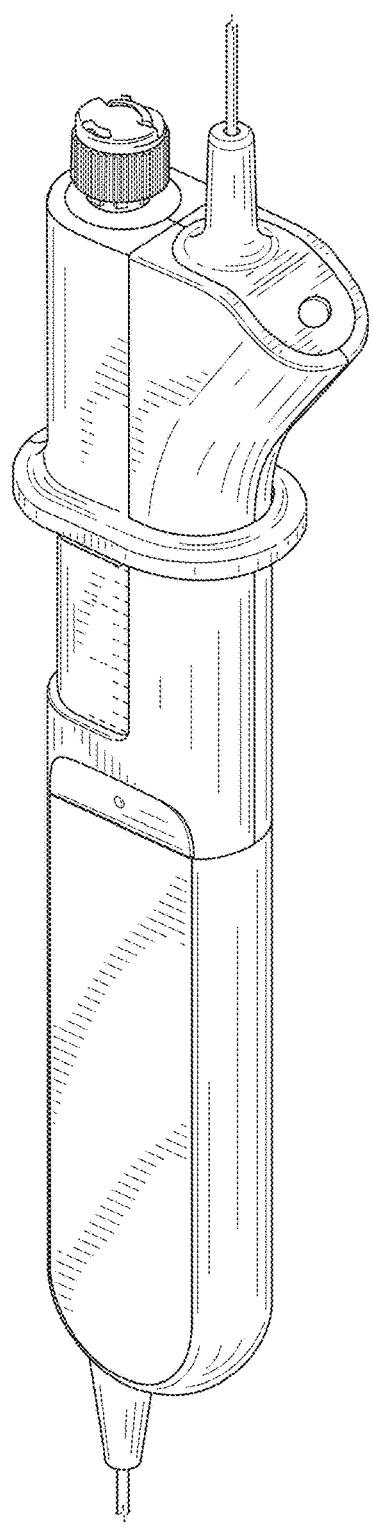
Figure 11D:
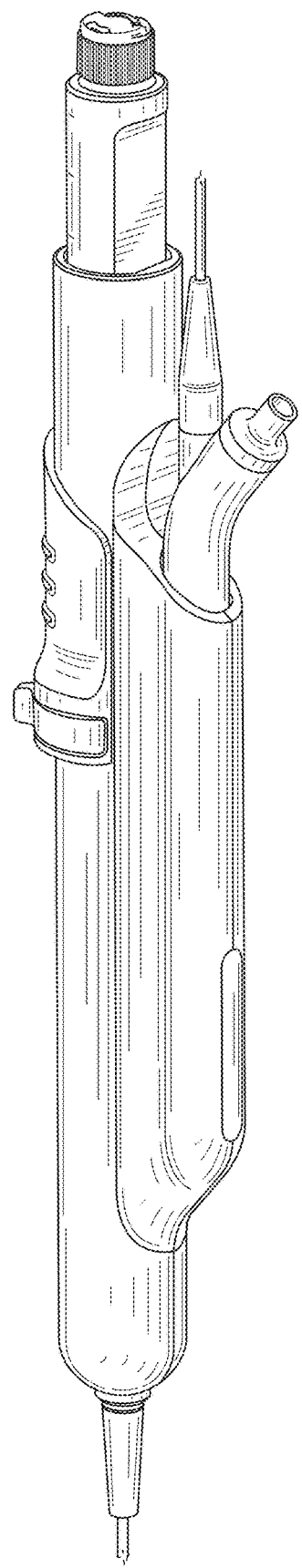
Figure 11G:
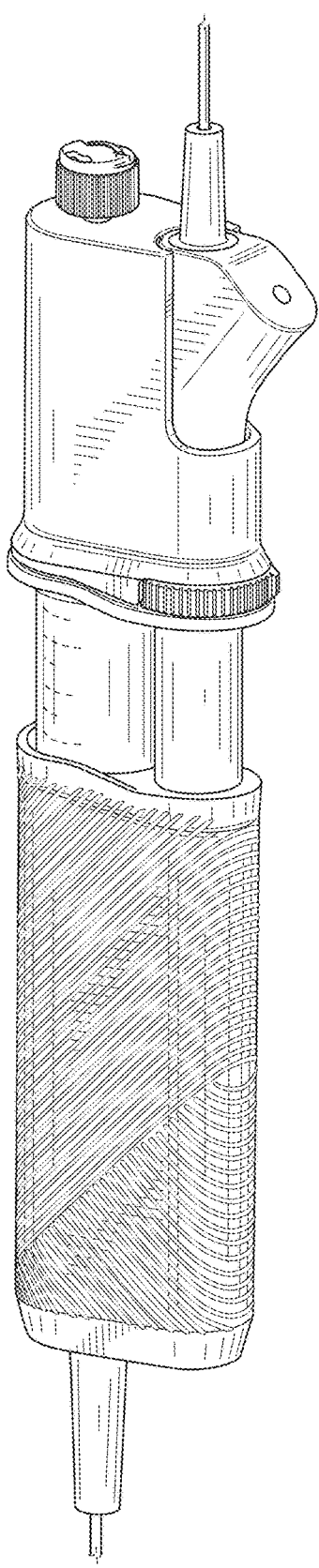
Figure 11H:
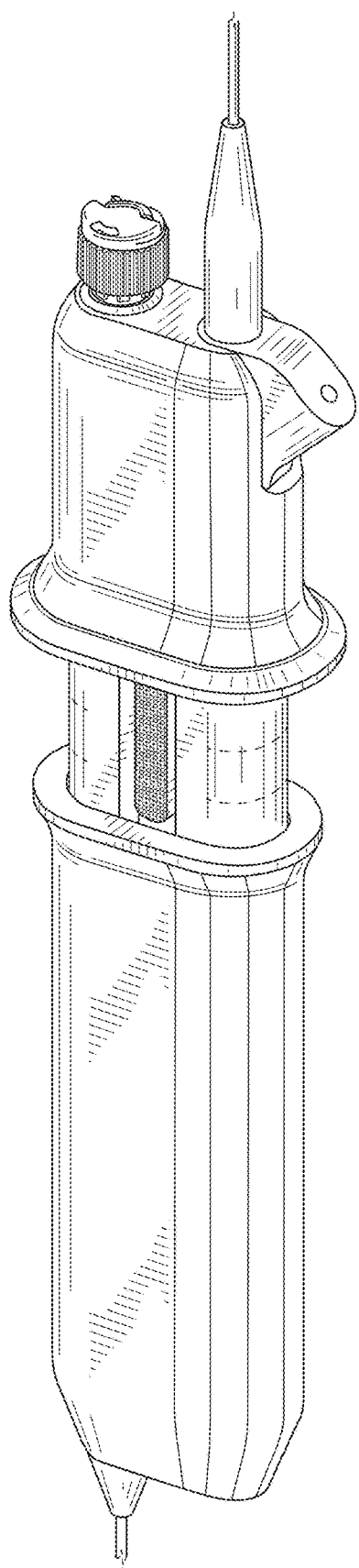
Figures 11I, 11J:
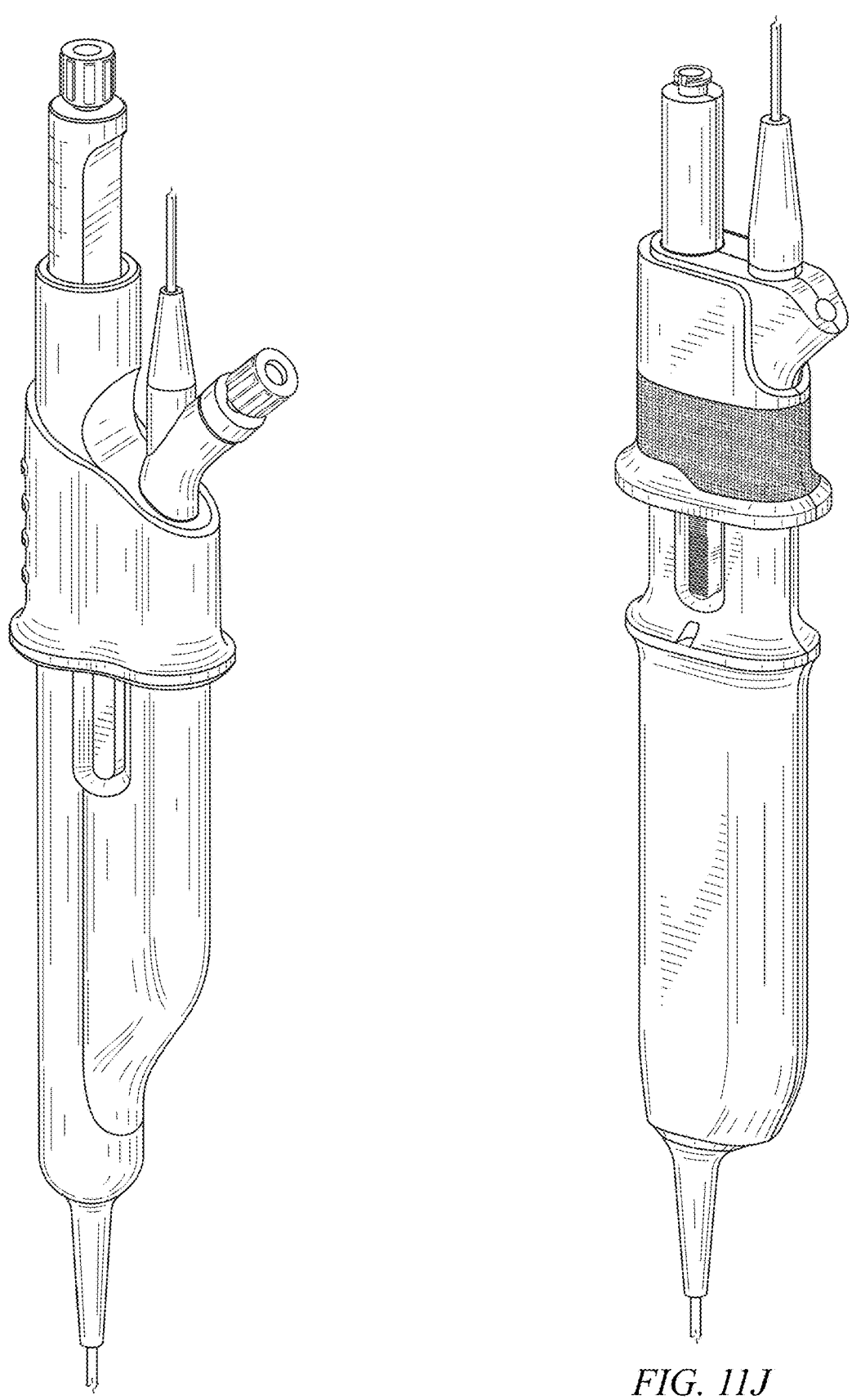
Figure 11K:
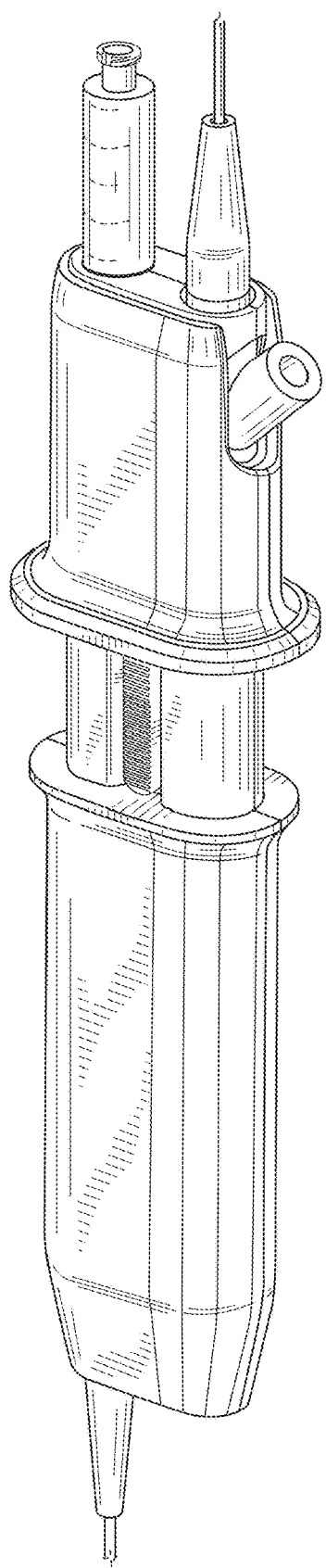
Figure 11L:
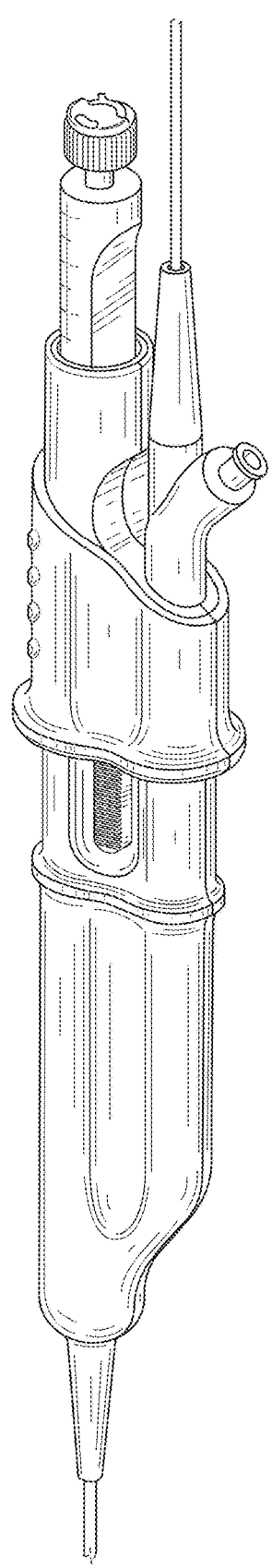

FIGS. 11A-11L illustrate various exemplary handle assemblies according to one or more embodiments described herein. More specifically, FIG. 11A illustrates a first handle assembly, FIG. 11B illustrates a second handle assembly, FIG. 11C illustrates a third handle assembly, FIG. 11D illustrates a fourth handle assembly, FIG. 11E illustrates a fifth handle assembly, FIG. 11F illustrates a sixth handle assembly, FIG. 11G illustrates a seventh handle assembly, FIG. 11H illustrates an eighth handle assembly, FIG. 11I illustrates a ninth handle assembly, FIG. 11J illustrates a tenth handle assembly, FIG. 11K illustrates an eleventh handle assembly, and FIG. 11L illustrates a twelfth handle assembly. Various aspects and features of one or more of the handle assemblies may be determined and/or combined based on particular application without departing from the scope of this disclosure. For example, features of a handle assembly may be selected based on hand dominance or size. Embodiments are not limited in this context.

As shown in FIG. 11B, in various embodiments, the distal strain relief may flow out of the main body while maintaining a clean bottom profile. Additionally, or alternatively, clean geometric intersections may be utilized to create part breaks and/or visual hierarchy. In some embodiments, the needle module (e.g., plunger assembly) may enter the handle body in the down position. In many embodiments, the sliding button (e.g., actuation member) may include a sculpted finger ridge. Further, a sliding button may be included on both sides of the handle body. In one or more embodiments, the grip zone may visually extend into the strain relief. The tool lock (slider below flush port) may include a graphical indicator. The grip zone may be textured and/or rubberized.

As shown in FIG. 11C, in various embodiments, the strain relief may be integrated into an overmolded side grip. Further, the tool lock (component on face with small circle in the middle) may be actuated front to back (e.g., similar to FIGS. 5C-5E). Further, the displacement gauge may be positioned for easy read out during actuation. In many embodiments, components, such as the displacement gauge, may be colored differently to increase visibility. For example, color changes may be used for visual separation of functional modules (e.g., plunger assembly and flush port assembly). As shown in FIG. 11D, in some embodiments, the tool lock (knob on opposite side of flush port below grip ribs) may be locked/unlocked with a rotational movement. As shown in FIG. 11E, in various embodiments, a pronounced needle assembly may provide ready access to the stylet (e.g., via the stylet cap). Additionally, or alternatively, the actuation member may include a textured (e.g., cross-hatched surface).

As shown in FIG. 11F, several embodiments may include a molded slider (actuation member) with a protruding center ridge, which may improve grip and/or reachability. Additionally, or alternatively, the distal end of the handle on the flush port side may include a rubberized, ergonomic grip zone with a sculpted hilt detail. In several embodiments, the handle body may taper towards the distal end, such as to provide a more natural grip zone. As shown in FIG. 11G, various embodiments may include a twist lock (e.g., rotatable disc below flush port). As shown in FIG. 11F, many embodiments may include tool lock that is recessed, such as to prevent inadvertent actuation. Additionally, or alternatively, embodiments may include a faceted grip zone (e.g., flush port assembly side).

One or more components described herein may be constructed from an elastomer and/or a polymer (e.g. polycarbonate, acrylonitrile butadiene styrene (ABS), high-density polyethylene (HDPE), Nylon, polyether ether ketone (PEEK), silicone, thermoplastic, plastic, or the like). Various components described herein may be constructed from a metal (e.g., stainless steel, titanium, aluminum, alloys, or the like). For example, port interface 882 may be constructed from a polymer and housing 810 may be constructed from nitinol. In another example, endcap 340 may be constructed from a polymer while distal juncture 348 and collar 342 are constructed from stainless steel. In yet another example, the layer of braid 360 may be constructed from metal while the lay of reflow 361 comprises a polymer. Other medical imaging related techniques, features, and/or components that may be used herein are disclosed in U.S. Non-Provisional patent application titled "Devices to Access Peripheral Regions of the Lung for Direct Visualization with Tool Attachment", U.S. Non-Provisional patent application Ser.No. 16/875,371, filed even date herewith, the entirety of which is incorporated herein by reference, and/or U.S. Non-Provisional patent application Ser. No. titled "Apparatus to Provide an Adjustable Mechanism for Radial Ultrasound Port and Flush Port", filed even date herewith, the entirety of which is incorporated herein by reference, and/or U.S. Non-Provisional patent application titled "Apparatus to Provide an Adjustable Mechanism for Radial Ultrasound Port and Flush Port", U.S. Non-Provisional patent application Ser. No. 16/875,382, filed even date herewith, the entirety of which is incorporated herein by reference.

The medical devices of the present disclosure are not limited to bronchoscopes, and may include a variety of medical devices for accessing body passageways, including, for example, catheters, ureteroscopes, duodenoscopes, colonoscopes, arthroscopes, cystoscopes, hysteroscopes, and the like. Further, in some embodiments, reference to endoscopy, endoscopic, endoscope etc. may generally refer to any medical device inserted into a body lumen. In one or more embodiments, a body passageway may be accessed for a biopsy procedure. For instance, a bronchoscope may be inserted into a patient for a lung nodule biopsy procedure (the location of the lung nodule may have been previously determined, such as based on virtual mapping and/or radiology). Once the bronchoscope is positioned, the medical imaging device may be inserted through a working channel and out past the distal end of the bronchoscope (e.g., 15 centimeters). The imaging transducer may then be activated inside the airway to provide real-time imaging of the lung nodule. Based on real-time imaging of the lung nodule and the marker indications, the medical imaging device may be positioned to biopsy the lung nodule. Once positioned, the biopsy needle may be actuated one or more times to take one or more core samples within the hollow biopsy needle. Further, suction and aspiration through the needle may be used to remove the sample(s) from the hollow biopsy needle. Additionally, one or more steps of this process may be repeated as necessary in the same or other locations of the nodule, and/or in other locations of the same lung airway or of other airways of the lungs.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
   a plunger assembly coupled to a first tool, the plunger assembly configured to move the first tool in a distal and a proximal direction within a first lumen;
   a flush port assembly coupled to a second tool, the flush port assembly configured to rotate, at least partially, about a longitudinal axis of the second tool independently of the plunger assembly, the flush port assembly coupled to a second lumen;
   a handle body connecting the plunger assembly to the flush port assembly, the handle body comprising a bifurcation joint, the bifurcation joint arranged to couple the first lumen and the second lumen to a dual-lumen catheter with first and second lumens;

a tool lock configured to prevent the plunger from moving the first tool in the distal and proximal directions when engaged; and a probe attached to a distal end of the dual-lumen catheter, wherein the probe includes a third lumen aligned with the first lumen of the dual-lumen catheter and a fourth lumen aligned with the second lumen of the dual-lumen catheter, wherein the plunger assembly and the flush port assembly are parallel to one another and are both disposed within the handle body.

2. The medical device of claim 1, wherein the flush port assembly can rotate at least 180 degrees about the longitudinal axis of the second tool.

3. The medical device of claim 1, wherein the first tool comprises a biopsy needle and the second tool comprises a radial ultrasound probe.

4. The medical device of claim 1, wherein the bifurcation joint connects the plunger assembly to a first lumen of the dual-lumen catheter and the flush port assembly to a second lumen of the dual-lumen catheter.

5. The medical device of claim 1, wherein the first tool is disposed in the first lumen and the second tool is disposed in the second lumen.

6. The medical device of claim 1, wherein the probe is attached to the distal end of the dual-lumen catheter via a reflow process.

7. The medical device of claim 1, wherein the second tool comprises an imaging transducer configured to communicatively couple with an imaging controller via a hub assembly.

8. The medical device of claim 1, wherein the handle body comprises at least two contours disposed along a horizontal axis on the handle body that are symmetrical, complementary, and/or mirrored.

9. The medical device of claim 7, wherein the imaging transducer is coupled to the hub assembly via a proximal drive cable with a first diameter and a distal drive cable with a second diameter, the first diameter larger than the second diameter.

10. The medical device of claim 9, wherein an impedance compensator connects the distal drive cable to the proximal drive cable.

11. The medical device of claim 9, wherein the imaging controller is coupled to the imaging transducer via the hub assembly and a coaxial cable.

* * * * *